US010441560B2

(12) United States Patent
Harada et al.

(10) Patent No.: US 10,441,560 B2
(45) Date of Patent: Oct. 15, 2019

(54) COMPOSITIONS AND METHODS FOR TREATING NON-ALCOHOLIC STEATOHEPATITIS

(71) Applicant: Mochida Pharmaceutical Co. LTD, Tokyo (JP)

(72) Inventors: Tsuyoshi Harada, Tokyo (JP); Hideo Kanehiro, Tokyo (JP); Kiyoshi Mizuguchi, Tokyo (JP)

(73) Assignee: Mochida Pharmaceutical Co., LTD., Tokyo (JP)

( * ) Notice: Subject to any disclaimer, the term of this patent is extended or adjusted under 35 U.S.C. 154(b) by 0 days.

(21) Appl. No.: 14/209,964

(22) Filed: Mar. 13, 2014

(65) Prior Publication Data

US 2015/0051143 A1 Feb. 19, 2015

Related U.S. Application Data

(60) Provisional application No. 61/793,309, filed on Mar. 15, 2013, provisional application No. 61/791,533, filed on Mar. 15, 2013.

(51) Int. Cl.

| A61K 31/232 | (2006.01) |
| A61K 45/06 | (2006.01) |
| A61K 9/107 | (2006.01) |
| A61K 47/10 | (2017.01) |
| A61K 47/24 | (2006.01) |
| A61K 47/44 | (2017.01) |

(52) U.S. Cl.
CPC ............ *A61K 31/232* (2013.01); *A61K 9/107* (2013.01); *A61K 45/06* (2013.01); *A61K 47/10* (2013.01); *A61K 47/24* (2013.01); *A61K 47/44* (2013.01)

(58) Field of Classification Search
None
See application file for complete search history.

(56) References Cited

U.S. PATENT DOCUMENTS

| 3,692,895 A | 9/1972 | Nelson et al. |
| 4,379,785 A | 4/1983 | Weyer et al. |
| 4,572,912 A | 2/1986 | Yoshioka et al. |
| 4,579,730 A | 4/1986 | Kidron et al. |
| 4,639,436 A | 1/1987 | Junge et al. |
| 4,849,405 A | 7/1989 | Ecanow |
| 4,904,769 A | 2/1990 | Rauenbusch |
| 4,963,526 A | 10/1990 | Ecanow |
| 5,019,508 A | 5/1991 | Johnson et al. |
| 5,594,016 A | 1/1997 | Ueno et al. |
| 5,614,492 A | 3/1997 | Habener |
| 5,642,868 A | 7/1997 | Talmy et al. |
| 5,703,188 A | 12/1997 | Mandeville et al. |
| 5,763,396 A | 6/1998 | Weiner et al. |
| 5,824,638 A | 10/1998 | Burnside et al. |
| 5,843,866 A | 12/1998 | Parket et al. |
| 6,153,632 A | 11/2000 | Rieveley |
| 6,191,105 B1 | 2/2001 | Ekwuribe et al. |
| 6,296,850 B1 | 10/2001 | Bjorklund et al. |
| 6,706,488 B2 | 3/2004 | Bjorklund et al. |
| 6,716,968 B2 | 4/2004 | Bjorklund et al. |
| 7,883,904 B2 | 2/2011 | Feldstein et al. |
| 7,897,591 B2 | 3/2011 | Puder et al. |
| 8,853,256 B2 | 10/2014 | Yokoyama et al. |
| 9,060,981 B2 | 6/2015 | Sato et al. |
| 9,486,433 B2 * | 11/2016 | Mizuguchi ........... A61K 31/232 |
| 10,058,528 B2 * | 8/2018 | Mizuguchi ........... A61K 31/232 |
| 2007/0218579 A1 | 9/2007 | Urdea et al. |
| 2008/0311593 A1 | 12/2008 | Younossi et al. |
| 2009/0297546 A1 | 12/2009 | Yamada et al. |
| 2011/0082119 A1 | 4/2011 | Yano |
| 2011/0092592 A1 | 4/2011 | Yano |
| 2011/0105510 A1 | 5/2011 | Ishikawa |
| 2012/0065264 A1 | 3/2012 | Fujii et al. |
| 2012/0231471 A1 | 9/2012 | Sato et al. |
| 2012/0264824 A1 | 10/2012 | Mizuguchi et al. |
| 2014/0057981 A1 * | 2/2014 | Fujii et al. .................... 514/549 |
| 2015/0247869 A1 | 9/2015 | Sato et al. |
| 2015/0258054 A1 * | 9/2015 | Mizuguchi ........... A61K 31/232 560/205 |
| 2016/0030378 A1 | 2/2016 | Harada et al. |

(Continued)

FOREIGN PATENT DOCUMENTS

| EP | 1582873 A1 | 10/2005 |
| EP | 1782807 A1 | 5/2007 |

(Continued)

OTHER PUBLICATIONS

MedIndia (downloaded online on Feb. 25, 2015 from URL:< http://www.medindia.net/patients/patientinfo/hba1c-blood-sugar-test. htm>).*
Cleveland Clinic (downloaded online on Feb. 26, 2015 from URL:< http://my.clevelandclinic.org/health/diagnostics/hic-blood-glucose-test>).*
Saebo (Pharma marine, downloaded online on Feb. 27, 2015 from URL:<www.calamarine.com>).*
Jeppesen et al, Relation of High TG-Low HDL Cholesterol and LDL Cholesterol to the Incidence of Ischemic Heart Disease (Arteriosclerosis, Thrombosis, and Vascular Biology. 1997; 17: 1114-1120).*

(Continued)

*Primary Examiner* — Sergio Coffa
(74) *Attorney, Agent, or Firm* — Wilson Sonsini Goodrich & Rosati, P.C.

(57) ABSTRACT

The disclosure provides for a method for treating a fatty liver disorder in a subject in need thereof, comprising selecting a subject having or suspected of having a fatty liver disease or disorder, wherein the subject is non diabetic, pre-diabetic, mildly diabetic, or has normal or substantially normal biliary tract function; and administering a therapeutically effective amount of a pharmaceutical composition comprising ethyl eicosapentanoate (EPA-E). In some cases EPA-E present may be at least 40% by weight in total of the fatty acids and their derivatives.

14 Claims, 19 Drawing Sheets

(56) References Cited

U.S. PATENT DOCUMENTS

| | | | |
|---|---|---|---|
| 2016/0213639 | A1 | 7/2016 | Suzuki et al. |
| 2017/0007566 | A1 | 1/2017 | Mizuguchi et al. |

FOREIGN PATENT DOCUMENTS

| | | | |
|---|---|---|---|
| EP | 2308493 A1 | | 4/2011 |
| EP | 2433630 A1 | | 3/2012 |
| EP | 2490026 A1 | | 8/2012 |
| EP | 2719382 A1 | | 4/2014 |
| JP | 2000-102399 A | | 4/2000 |
| JP | 2002-114768 A | | 4/2002 |
| JP | 2007-236253 A | | 9/2007 |
| JP | 2007-315752 A | | 12/2007 |
| JP | 2009-120607 A | | 6/2009 |
| JP | 2009-534317 A | | 9/2009 |
| JP | 2011-006380 A | | 1/2011 |
| JP | 2011-519846 A | | 7/2011 |
| JP | 2012-180337 A | | 9/2012 |
| WO | WO 85/05029 A1 | | 11/1985 |
| WO | WO 97/11345 A1 | | 3/1997 |
| WO | WO 98/05331 A2 | | 2/1998 |
| WO | WO 98/57652 A1 | | 12/1998 |
| WO | WO 99/58518 A2 | | 11/1999 |
| WO | WO 99/58521 A1 | | 11/1999 |
| WO | WO 99/58522 A1 | | 11/1999 |
| WO | WO 99/61435 A1 | | 12/1999 |
| WO | WO 02/26707 A1 | | 4/2002 |
| WO | WO 02/26743 A1 | | 4/2002 |
| WO | WO 03/032916 A2 | | 4/2003 |
| WO | WO 03/032982 A1 | | 4/2003 |
| WO | WO 03/041729 A1 | | 5/2003 |
| WO | WO 03/055883 A1 | | 7/2003 |
| WO | WO 2005/063231 A2 | | 7/2005 |
| WO | WO 2007/016390 A1 | | 2/2007 |
| WO | WO 2008/075788 A1 | | 6/2008 |
| WO | WO 2008/113177 A1 | | 9/2008 |
| WO | WO 2009/028457 A1 | | 3/2009 |
| WO | WO 2009/151116 A1 | | 12/2009 |
| WO | WO 2009/151125 A1 | | 12/2009 |
| WO | WO 2009/154230 A1 | | 12/2009 |
| WO | WO-2010004982 A1 | | 1/2010 |
| WO | WO2010134614 | * | 11/2010 |
| WO | WO-2011046204 A1 | | 4/2011 |
| WO | WO 2012/032417 A2 | | 3/2012 |
| WO | WO 2013/127728 A1 | | 9/2013 |
| WO | WO 2014/057522 A1 | | 4/2014 |
| WO | WO 2014/142364 A2 | | 9/2014 |
| WO | WO 2015/053379 A1 | | 4/2015 |

OTHER PUBLICATIONS

Capanni et al, Prolonged n-3 polyunsaturated fatty acid supplementation ameliorates hepatic steatosis in patients with non-alcoholic fatty liver disease: a pilot study, Aliment Pharmacol Ther 23, 1143-1151, 2006.*
Kajikawa, Eicosapentaenoic Acid Attenuates Progression of Hepatic Fibrosis with Inhibition of Reactive Oxygen Species Production in Rats Fed Methionine- and Choline-Deficient Diet (Dig Dis Sci. Apr. 2011;56(4):1065-74).*
Ahmed et al. (Asian J. Biochem., 7 (1): 16-26, 2012).*
Montenegro et al. (Gum Arabic: More Than an Edible Emulsifier, Products and Applications of Biopolymers, ISBN: 978-953-51-0226-7, 2012).*
Obika et al. (Exp. Diabetes Res. 2012: 2012:145754 (pub. Online Oct. 27, 2011)) (Year: 2011).*
American Diabetes Association and National Institute of Diabetes, Digestive, and Kidney Diseases. The prevention or delay of type 2 diabetes. Diabetes Care. Apr. 2002;25(4):742-9.
Carpentier, et al. n-3 fatty acids and the metabolic syndrome. Am J Clin Nutr. Jun. 2006;83(6 Suppl):1499S-1504S.
Chatzigeorgiou, et at. Plasma and urine soluble CD40 (sCD40) in children and adolescents with type 1 diabetes mellitus (T1DM). A possible pathway to diabetic angiopathy. FEBS Journal (2008), vol. 275 (Suppl. 1). PP7A-14, p. 303 (abstract).
Communication Pursuant to Article 94(3) EPC dated May 16, 2014, in European Patent Application No. 10823472.5.
Database Biosis (Online] Biosciences Information Services, Philadelphia. PA, US (Apr. 2006); Gurhen et at, The Effects of Atorvastatin on Hematological and Inflammatory Parameters,'XP002700442, Database Accession No. PREV200900258247—abstract'.
Database Biosis [Online) Bioscience Information Service, Philadelphia, PA, US (Nov. 2008): Cayon et al:, "Gene expression in obese patients with non-alcoholic steatonepatitis," XP002700444, Database Accession No. PREV200800490452 'abstract'.
Dennis. The growing phospholipase A2 superfamily of signal transduction enzymes. Trends Biochem Sci. Jan. 1997;22(1):1-2.
English translation of International Preliminary Report on Patentability and Written Opinion dated Apr. 17, 2012, in PCT International Application No. PCT/JP2010/068168.
Estep, et al. Expression of cytokine signaling genes in morbidly obese patients with non-alcoholic steatohepatitis and hepatic fibrosis. Obes Surg. May 2009;19(5):617-24. doi: 10.1007/s11695-009-9814-x. Epub Mar. 12, 2009.
European search report and opinion dated Mar. 4, 2013 for EP Application No. 12188329.2.
Extended European Search Report dated Jul. 23, 2012, in European Patent Application No. 10823472.5.
Forst, et al. Improved plaque stability and reduced inflammation during pioglitazone treatment in type 2 diabetic patients with CHD. Diabetes. Jun. 2007; vol. 55, Suppl. 1. 647-P, p. A172.
Forst, et al. Pleiotrophic and anti-inflammatory effects of pioglitazone precede the metabolic activity in type 2 diabetic patients with coronary artery disease. Atherosclerosis. Mar. 2008;197(1):311-7. Epub Jun. 22, 2007.
Haukeland, et al. Systemic inflammation in nonalcoholic fatty liver disease is characterized by elevated levels of CCL2. J Hepatol. Jun. 2006;44(6):1167-74. Epub Mar. 20, 2006.
Horie et al. Hepatocyte-specific pten deficiency results in steatohepatitis and hepatocellular carcinoma, and Insulin Hypersensitivity. Hepatology, Oct. 2004, No. 609, p. 428A.
International search report dated Jan. 25, 2011 for PCT/JP2010/068168.
International search report dated Nov. 20, 2012 for PCT/JP2012/006551.
Jin et al. Telmisartan prevents hepatic fibrosis and enzyme-altered lesions in liver cirrhosis rat induced by a choline-deficient L-amino acid-defined diet. Biochem Biophys Res Commun. Dec. 28, 2007;364(4):801-7. Epub Oct. 24, 2007.
Johannsson, et al. Growth hormone treatment of abdominally obese men reduces abdominal fat mass, improves glucose and lipoprotein metabolism, and reduces diastolic blood pressure. J Clin Endocrinol Metab. Mar. 1997;82(3):727-34.
Kleiner, et al. Design and validation of a histological scoring system for nonalcoholic fatty liver disease. Hepatology. Jun. 2005;41(6):1313-21.
Kudo, et al. Lipopolysaccharide triggered TNF-alpha-induced hepatocyte apoptosis in a murine non-alcoholic steatohepatitis model. J Hepatol. Jul. 2009;51(1):168-75. doi: 10.1016/j.jhep.2009.02.032. Epub May 3, 2009.
Kurita et al. Olmesartan ameliorates a dietary rat model of non-alcoholic steatohepatitis through its pleiotropic effects. Eur J Pharmacol. Jul. 7, 2008;588(2-3):316-24. doi: 10.1016/j.ejphar.2008.04.028. Epub Apr. 16, 2008.
Mason, et al. Effect of enhanced glycemic control with saxagliptin on endothelial nitric oxide release and CD40 levels in obese rats. J Atheroscler Thromb. 2011;18(9):774-83. Epub Jun. 13, 2011.
Meigs, et al. The natural history of progression from normal glucose tolerance to type 2 diabetes in the Baltimore Longitudinal Study of Aging. Diabetes. Jun. 2003;52(6):1475-84.
Neuschwander-Tetri, et al. Nonalcoholic steatohepatitis: summary of an AASLD Single Topic Conference. Hepatology. May 2003;37(5):1202-19.
Notification of Reasons for Refusal dated Nov. 4, 2014, in Japanese Patent Application No. 2011-536192, with English translation.
Office action dated Feb. 11, 2013 for U.S. Appl. No. 13/088,072.

(56) References Cited

OTHER PUBLICATIONS

Office action dated Feb. 11, 2013 for U.S. Appl. No. 13/500,753.
Office action dated Aug. 13, 2013 for U.S. Appl. No. 13/088,072.
Office action dated Nov. 12, 2014 for U.S. Appl. No. 13/500,753.
Office action dated Nov. 21, 2014 for U.S. Appl. No. 13/088,072.
Schmilovitz-Weiss et al. Role of circulating soluble CD40 as an apoptotic marker in liver disease. Apoptosis. Mar. 2004;9(2):205-10.
Tamimi, et al. An apoptosis panel for nonalcoholic steatohepatitis diagnosis. J Hepatol. Jun. 2011;54(6):1224-9. doi: 10.1016/j.jhep.2010.08.023. Epub Feb. 12, 2011.
Tanaka, et al. Highly purified eicosapentaenoic acid treatment improves nonalcoholic steatohepatitis. J Clin Gastroenterol. Apr. 2008;42(4):413-8. doi: 10.1097/MCG.0b013e31815591aa.pp. 413-418.
The Japan Society of Hepatology ed., "NASH • NAFLD no Shinryo Gaido (Guidelines for Diagnosis and Treatment of NASH and NAFLD)", Bunkodo Co., Ltd., Aug. 22, 2006, and its partial translation.
Valva, et al. Apoptosis markers in liver biopsy of nonalcoholic steatohepatitis in pediatric patients. Hum Pathol. Dec. 2008;39(12):1816-22. doi: 10.1016/j.humpath.2008.04.022. Epub Aug. 20, 2008.
Varma, et al. Thrombospondin-1 is an adipokine associated with obesity, adipose inflammation, and insulin resistance. Diabetes. Feb. 2008;57(2):432-9. Epub Dec. 5, 2007.
Varo, et al. Elevated plasma levels of the atherogenic mediator soluble CD40 ligand in diabetic patients: a novel target of thiazolidinediones. Circulation. Jun. 3, 2003;107(21):2664-9. Epub May 12, 2003.
Yener, et al. Plasminogen activator inhibitor-1 and thrombin activatable fibrinolysis inhibitor levels in non-alcoholic steatohepatitis. J Endocrinol Invest. Nov. 2007;30(10):810-9. Abstract only.
Yoneda, et al. Plasma Pentraxin3 is a novel marker for nonalcoholic steatohepatitis (NASH). BMC Gastroenterol. Nov. 14, 2008;8:53. doi: 10.1186/1471-230X-8-53.
Notice of allowance dated Jul. 25, 2016 for U.S. Appl. No. 14/435,121.
Notarnicola, et al. Increased serum levels of lipogenic enzymes in patients with severe liver steatosis. Lipids Health Dis. Oct. 30, 2012;11:145. doi: 10.1186/1476-511X-11-145.
Office action dated Sep. 7, 2016 for U.S. Appl. No. 14/775,452.
Office action dated Oct. 6, 2016 for U.S. Appl. No. 13/088,072.
Yilmaz, et al. Serum M30 levels: a potential biomarker of severe liver disease in nonalcoholic fatty liver disease and normal aminotransferase levels. Hepatology. Feb. 2009;49(2):697; author reply 697. doi: 10.1002/hep.22691.
Farrell, et al. NASH is an Inflammatory Disorder: Pathogenic, Prognostic and Therapeutic Implications. Gut Liver. Apr. 2012;6(2):149-71. doi: 10.5009/gnl.2012.6.2.149. Epub Apr. 17, 2012.
Nemoto, et al. Ethyl-eicosapentaenoic acid reduces liver lipids and lowers plasma levels of lipids in mice fed a high-fat diet. In Vivo. Sep.-Oct. 2009;23(5):685-9.
Office action dated Apr. 19, 2016 for U.S. Appl. No. 14/775,452.
Office action dated Apr. 27, 2016 for U.S. Appl. No. 14/435,121.
U.S. Appl. No. 14/914,444, filed Feb. 25, 2016, Suzuki et al.
Lee, et al. Comparison of methods to measure low serum estradiol levels in postmenopausal women. J Clin Endocrinol Metab. Oct. 2006;91(10):3791-7. Epub Aug. 1, 2006.
Nichols, et al. From menarche to menopause: trends among US Women born from 1912 to 1969. Am J Epidemiol. Nov. 15, 2006;164(10):1003-11. Epub Aug. 23, 2006.
Office action dated Nov. 16, 2015 for U.S. Appl. No. 14/435,121.
U.S. Appl. No. 14/435,121, filed Apr. 10, 2015, Mizuguchi et al.
U.S. Appl. No. 14/714,766, filed May 18, 2015, Sato et al.
Armutcu, et al. Thymosin alpha 1 attenuates lipid peroxidation and improves fructose-induced steatohepatitis in rats. Clin Biochem. Jun. 2005;38(6):540-7.
Feldstein, et al. Hepatocyte apoptosis and fas expression are prominent features of human nonalcoholic steatohepatitis. Gastroenterology. Aug. 2003;125(2):437-43.
Hanniman, et al. Apolipoprotein A-IV is regulated by nutritional and metabolic stress: involvement of glucocorticoids, HNF-4 alpha, and PGC-1 alpha. J Lipid Res. Nov. 2006;47(11):2503-14. Epub Aug. 23, 2006.
International preliminary report on patentability and written opinion dated Nov. 20, 2012 for PCT Application No. JP2012/006551.
International search report and written opinion dated Dec. 16, 2014 for PCT Application No. JP2014/077120.
Kajikawa, et al. Eicosapentaenoic acid attenuates progression of hepatic fibrosis with inhibition of reactive oxygen species production in rats fed methionine- and choline-deficient diet. Digestive Diseases and Sciences, 201, vol. 56, No. 4, p. 1065-1074.
Kajikawa, et al. Highly Purified Eicosapentaenoic Acid Ethyl Ester Prevents Development of Steatosis and Hepatic Fibrosis in Rats. Digestive Diseases and Sciences, 2010, vol. 55, No. 3, p. 631-641.
Kan Tan Sui. 2010, vol. 60, No. 5, p. 759-764.
Kanzo. 2002, vol. 43, No. Supplement 2, p. A397.
Kanzo. 2005, vol. 46, No. Supplement 2, p. A329.
Kanzo. vol. 53, No. Supplement 2, 212, p. A706.
Kawashima, et al. Preventive Effects of Highly Purified Eicosapentaenoic Acid on Development of Steatosis and Hepatic Fibrosis Induced by a Methionine- and Choline-Deficient Diet in Rats. Gastroenterology, 2009, vol. 136, No. 5, p. A804.
Mitsuhashi, H. [Thrombo test (TBT, hepaplastin test (HPT)]. Nihon Rinsho. Dec. 2004;62 Suppl 12:594-6.
National Institutes of Health (NIH) National Institute of Diabetes and Digestive and Kidney Diseases, "Nonalcoholic Steatohepatitis", Nov. 2006.
Notice of allowance dated Feb. 20, 2015 for U.S. Appl. No. 13/500,753.
Obstetrical and Gynecological Practice. vol. 56, No. 8, 2007, p. 1161-1165.
Oestvang, et al. PhospholipaseA2: a key regulator of inflammatory signalling and a connector to fibrosis development in atherosclerosis. Biochim Biophys Acta. Nov. 2006;1761(11):1309-16. Epub Jul. 1, 2006.
Office action dated Jul. 20, 2015 for U.S. Appl. No. 13/088,072.
Proceedings of the 61st meeting of Japan Society of Home Economics. 2009, vol. 61st, p. 32.
Proceedings of the 65th Annual meeting of the Japan Society of Nutrition and Food Science. 2011, vol. 65th, p. 110.
Sawada, et al. [NASH model—role of interleukin-1 receptor]. Nihon Rinsho. Jun. 2006;64(6):1063-70.
Schlemmer, et al. Oestrogen and essential fatty acid supplementation corrects bone loss due to ovariectomy in the female Sprague Dawley rat. Prostaglandins Leukot Essent Fatty Acids. vol. 61, No. 6, 1999, pp. 381-390.
Tirosh, et al. Nutritional lipid-induced oxidative stress leads to mitochondrial dysfunction followed by necrotic death in FaO hepatocytes. Nutrition. Feb. 2009;25(2):200-8. doi: 10.1016/j.nut.2008.07.023. Epub Oct. 22, 2008.
Watanabe, et al. Hepatology Oct. 2004, 428A, 609.
Anty, R., A new composite model including metabolic syndrome, alanine aminotransferase and cytokeratin-18 for the diagnosis of non-alcoholic steatohepatitis in morbidly obese patients. Aliment Pharmacol Ther. Dec. 2010;32(11-12):1315-22. doi: 10.1111/j.1365-2036.2010.04480.x. Epub Oct. 7, 2010.
Bauer, et al., Connective tissue growth factor level is increased in patients with liver cirrhosis out is not associated with complications or extent of liver injury. Regulatory peptides. 2012, 179(1-3):10-14.
Brown, TT. et al., Association between systemic inflammation and incident diabetes in HIV-infected patients after initiation of antiretroviral therapy. Diabetes Care. Oct. 2010;33(10):2244-9. doi: 10.2337/dc10/0633. Epub Jul. 27, 2010.
Ciprandi, G. et al., Serum adipsin levels in patients with seasonal allergic rhinitis: preliminary data.Int Immunopharmacol. Nov. 2009;9(12):1460-3. doi: 10.1016/j.intimp.2009.08.004. Epub Aug. 20, 2009.
Florentino, et al., Nonalcoholic fatty liver disease in menopausal women. Arquivos de gastroenterologia. 2013;50(3): p. 180-185.
Gomolka, B. et al., Analysis of omega-3 and omega-6 fatty acid-derived lipid metabolite formation in human and mouse blood

(56) References Cited

OTHER PUBLICATIONS samples. Prostaglandins Other Lipid Mediat. Apr. 2011;94(3-4):81-7. doi: 10.1016/j.prostaglandins.2010.12.006. Epub Jan. 12, 2011.

Hosoyamada, K. et al., Fatty liver in men is associated with high serum levels of small, dense low-density lipoprotein cholesterol. Diabetol Metab Syndr. Jul. 18, 2012;4(1):34.

Kalhan, SC. et al., Plasma metabolomic profile in nonalcoholic fatty liver disease. Metabolism. Mar. 2011;60(3):404-13. doi: 10.1016/j.metabol.2010.03.006. Epub Apr. 27, 2010.

Lanfear, DE. et al., Short term effects of milrinone on biomarkers of necrosis, apoptosis, and inflammation in patients with severe heart failure.J Transl Med. Jul. 29, 2009;7:67. doi: 10.1186/1479-5876-7-67.

Lee, H. et al., Diagnostic Significance of Serum HMGB1 in Colorectal Carcinomas. 2012.PLoS One 7(4): e34318. doi:10.1371/journal.pone.0034318.

Lowe, GDO. et al., Blood viscosity and risk of cardiovascular events: the Edinburgh Artery Study. British Journal of Haematalogy. 1997.96: 168-173.

Nakajima, K. et al., The characteristics of remnant lipoproteins in the fasting and postprandial plasma.Clinica Chimica Acta; International Journal of Clinical Chemistry [2012, 413(13-14):1077-1086].

Office Action dated Jan. 13, 2017 for U.S. Appl. No. 14/914,444.

Rabelo, F. et al., Pro- and anti-inflammatory cytokines in steatosis and steatohepatitis. Obes Surg. Jul. 2010;20(7):906-12. doi: 10.1007/s11695-010-0181-4.

Schmilovitz-Weiss, H. et al., Role of circulating soluble CD40 as an apoptotic marker in liver disease. Mar. 2004, vol. 9, Issue 2, pp. 205-210.

Sumida, Y. et al., Serum thioredoxin levels as a predictor of steatohepatitis in patients with nonalcoholic fatty liver disease. J Hepatol. Jan. 2003;38(1):32-8.

Tavares De Almeida, I. et al., Plasma total and free fatty acids composition in human non-alcoholic steatohepatitis. Jun. 21, 2002(3). 219-223.

Zimmermann, E. et al., C-reactive protein levels in relation to various features of non-alcoholic fatty liver disease among obese patients. J Hepatol. Sep. 2011;55(3):660-5. doi: 10.1016/j.jhep.2010.12.017. Epub Jan. 14, 2011.

European Search Report dated Feb. 8, 2017 for EP Application No. 14852793.0.

Office Action dated Apr. 19, 2017 for U.S. Appl. No. 14/775,452.

Witt, P.M. et al., The incorporation of marine n-3 PUFA into platelets and adipose tissue in pre- and postmenopausal women: a randomised,double-blind, placebo-conrolled trial. British journal of nutrition. 104; 2010: 318-325.

Notice of Allowance dated Oct. 18, 2017 for U.S. Appl. No. 14/775,452.

Office Action dated Oct. 5, 2017 for U.S. Appl. No. 14/714,766.

EPADEL Capsules 300—An EPA Preparation, Apr. 2011 (7th Version) with Translation, 4 pages.

Office Action dated Aug. 16, 2017 for U.S. Appl. No. 15/269,134.

Di Minno, et al., Omega-3 fatty acids for the treatment of non-alcoholic fatty liver disease. World J Gastroenterology, Nov. 7, 2012;18(41):5839-5847.

TW103131236 Office Action dated Jul. 10, 2018 (w/ English translation).

Kamada, et al., Estrogen deficiency worsens steatohepatitis in mice fed high-fat and high-cholesterol diet. Am J Physiol Gastrointest Liver Physiol, Sep. 2011; 301:G1031-G1043.

U.S. Appl. No. 14/775,452 Notice of Allowance dated Jan. 12, 2018.

U.S. Appl. No. 14/914,444 Office Action dated Jan. 22, 2018.

U.S. Appl. No. 15/269,134 Office Action dated May 15, 2018.

* cited by examiner

| Proportion of responder (n of responder/n of cases) | Placebo | EPA-E 1800mg/day |
|---|---|---|
| All Cases | 32.7% (18/55) | 32.7% (18/55) |
| Non-Diabetes | 27.5% (11/40) | 41.9% (13/31) |
| Non-Diabetes + Mild Diabetes (anti-diabetes agent ≦1) | 27.7% (13/47) | 37.8% (17/45) |

| p value by χ square test vs. Placebo | EPA-E 1800mg/day |
|---|---|
| All Cases | 1.000 |
| Non-Diabetes | 0.202 |
| Non-Diabetes + Mild Diabetes (anti-diabetes agent ≦1) | 0.301 |

Fig. 1

| Proportion of responder (n of responder/n of cases) | | Placebo | EPA-E 1800mg/day |
| --- | --- | --- | --- |
| All Cases | HbA1c=<6.4 | 23.7% (9/38) | 42.1%* (16/38) |
| Non-Diabetes | HbA1c=<6.4 | 22.9% (8/35) | 46.4%** (13/28) |

χ square test vs. Placebo  *: p<0.10   **: p<0.05

| p value by χ square test vs. Placebo | | EPA-E 1800mg/day |
| --- | --- | --- |
| All Cases | HbA1c=<6.4 | 0.087* |
| Non-Diabetes | HbA1c=<6.4 | 0.049** |

Fig. 2

| Proportion of responder (n of responder/n of cases) | | Placebo | EPA-E 1800mg/day |
|---|---|---|---|
| All Cases | Glucose=<125 | 25.6% (11/43) | 36.2% (17/47) |
| Diabetes | Glucose=<125 | 0.0% (0/5) | 22.2% (4/18) |
| Non-Diabetes | Glucose=<125 | 28.9% (11/38) | 44.8% (13/29) |

| p value by χ square test vs. Placebo | | EPA-E 1800mg/day |
|---|---|---|
| All Cases | Glucose=<125 | 0.278 |
| Diabetes | Glucose=<125 | 0.246 |
| Non-Diabetes | Glucose=<125 | 0.179 |

Fig. 3

| Proportion of responder (n of responder/n of cases) | | Placebo | EPA-E 1800mg/day |
|---|---|---|---|
| All Cases | HbA1c=<6.4 and Glucose=<125 | 22.9% (8/35) | 43.2%* (16/37) |
| Diabetes | HbA1c=<6.4 and Glucose=<125 | 0.0% (0/2) | 33.3% (3/9) |
| Non-Diabetes | HbA1c=<6.4 and Glucose=<125 | 24.2% (8/33) | 46.4%* (13/28) |

χ square test vs. Placebo    *: $p<0.10$

| p value by χ square test vs. Placebo | | EPA-E 1800mg/day |
|---|---|---|
| All Cases | HbA1c=<6.4 and Glucose=<125 | 0.067* |
| Diabetes | HbA1c=<6.4 and Glucose=<125 | 0.338 |
| Non-Diabetes | HbA1c=<6.4 and Glucose=<125 | 0.069* |

Fig. 4

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| ALT (6-41 U/L) | 10-300 | Lower limit range values of 10, 50, 100, 150, | at least 1% lower | 1 to about 95% reduction |

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| | | or 200, upper limit range values of 100, 150, 200, 250, or 300, ranges of 10-300, 10-250, 10-150, 10-100, 100-200, 200-300 | | |
| AST (9-34 U/L) | 10-250 | Lower limit range values of 10, 50, 100, 150, or 200, upper limit range values of 100, 150, 200, 250, or 300, ranges of 10-300, 10-250, 10-150, 10-100, 100-200, 200-300 | at least 1% lower | 1 to about 95% reduction |
| AST/ALT ratio | | upper limit range values of 0.5, 0.7, 0.8, 1, 1.2, 2, ranges of 0.5-2, 0.8-1-1.2 | | |
| alkaline phosphatase (ALP) (80-260 IU/L) | 80-300 | ranges of 80-800 | no worsening | no worsening, 1 to about 90% reduction, 300 IU/L or less, 250 IU/L or less |
| Total bilirubin (0.2-1.2 mg/dL) | | | no worsening | no worsening, 1 to about 90% reduction |
| Gamma-Glutamyl Transferase (GGT or γGTP) (males: 5-40 U/L) | | | no worsening | no worsening, 1 to about 90% reduction, 100 U/L or less, 70 U/L or less |
| Albumin (3.8-5.2 g/dl) | | | no worsening | no worsening, 1 to about 90% increase, ranges of 3-6 g/dl, 3.5-5.5 g/dl |
| HDL-C (high density lipoprotein cholesterol) (35-60 mg/dl) | less than 55 | less than 60 mg/dl, 55, 50, 45, 40, 35, 30, 25, or 20 mg/dl, ranges of 25-55, 30-40 mg/dl, 40-50 mg/dl, 50-60 mg/dl, at least 60 | no worsening, at least 1% increase | no change, 1-90% increase, 40 mg/dl or more |
| LDL-C (low density lipoprotein cholesterol) (50-130 mg/dl) | 100-200 | at least 70 mg/dl, 100, 120, 130, 140, 150, 170, 180, or 200 or a range of 70-300, 70-250, 70-200, 100-250, 100-200, 130-200, 140-180, 100-150, 130-160, 160-180 | no worsening | no change, 1-90% reduction less than 160 mg/dl, 140, 130, 120, 100, 70 mg/dl |

Fig. 5

| Item (Typical Normal Values, Units) | Pre-treatment baseline Typical Range(s) | Pre-treatment baseline Observable Ranges or Values | After dosing (effect) values Typical Range(s) | After dosing (effect) values Observable Ranges or Values |
|---|---|---|---|---|
| Triglycerides (TG) (fed or fasting, 80-150 mg/dl) | 100-1000 | at least 80 mg/dl, 100, 150, 180, 200, 300, 500, 750, 1000, 1200, or 1500, or less than 150, or a range of 100-2500, 100-1500, 100-1000, 150-500, 200-500, 150-300, 150-200, 200-500 | at least 1% lower | 1 to about 90% reduction, 500 mg/dl or less, 300, 200, 150, 100 mg/dl or less |
| Total Cholesterol (TC) (100-200 mg/dl) | 170-300 | a range of 130-300 mg/dl, 200-220, 220-240, 240-260, or at least 260, or less than 260 mg/dl | no worsening | no change, 1-90% reduction |
| TG and HDL-C | High TG and low HDL-C (ex. TG ≧ 150 mg/dl and HDL ≦ 40 mg/dl) | TG: at least 150, 200, 500 mg/dl HDL-C: less than 40, 50 mg/dl | no worsening | |
| TG/HDL-C ratio | at least 3.75 | at least 2, 2.5, 3, 3.75, 4, 5, 10, or ranges of 2-3.75, 3.75-10 | at least 1% lower | no worsening, at least 1% lower, or 1-90% reduction |
| Non-HDL-C (mg/dl) | at least 130 | at least 100 mg/dl, 130, 150, 160, 170, 190, a range of 100 to 250 | no worsening | no worsening, or at least 1% lower, or less than 130 mg/dl, 150, 160, 170, 190 |
| Free fatty acid (μ Eq/l) (140-850) | at least 400 | less than 400, at least 400, 600, 800, 1000 | at least 1% lower | no change, or at least 1 to 90% reduction |
| Eicosapentaenoic Acid/Arachidonic Acid (EPA/AA) (ex. (mol%)/(mol%)) | less than 0.5/low compared to average level of normal subjects | less than 1, 0.75, 0.5, 0.1, ranges of 0.01-2 | at least 5% increase | 5 to about 200% increase, about 2-200-fold increase |
| Arachidonic Acid (AA) (ex. mol%) | High compared to average level of normal subjects | | at least 1% lower | no change, 1 to about 90% reduction |
| Eicosapentaenoic Acid (EPA) (ex. mol%) | low compared to average level of normal subjects | | at least 5% increase | 5 to about 200% increase, about 2-500-fold increase |
| Docosapentaenoic Acid (DPA) (ex. mol%) | low compared to average level of normal subjects | | at least 1% increase | 1 to about 90% increase |
| Docosahexaenoic Acid (DHA) (ex. mol%) | low compared to average level of normal subjects | | | |
| DPA/AA ratio | low compared to average level of normal subjects | | | |

Fig. 5
(continued)

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| DPA/AA ratio | low compared to average level of normal subjects | | | |
| DHA/DPA ratio | low compared to average level of normal subjects | | | |
| Monounsaturated fatty acid (MUFA) (ex. mol%) | High compared to average level of normal subjects | | at least 1% lower | no change, at least 1% lower |
| Palmitoleic acid (16:1 n7) (ex. mol%) | High compared to average level of normal subjects | | at least 1% lower | no change, at least 1% lower |
| Oleic acid (18:1 n9) (ex. mol%) | High compared to average level of normal subjects | | at least 1% lower | no change, a least 1% lower |
| Oleic acid (18:1 n9)/ stearic acid (18:0) ratio | High compared to average level of normal subjects | | at least 1% lower | no change, at least 1% lower |
| Palmitoleic acid (16:1)/ Palmitic acid (16:0) ratio | High compared to average level of normal subjects | | at least 1% lower | no change, at least 1% lower |
| Stearic acid (18:0)/ Palmitic acid (16:0) ratio | High compared to average level of normal subjects | | no change, or at least 1% lower | no change, or at least 1% lower |
| γ-linoleic acid (18:3 n6)/ Linoleic acid (18:2 n6) ratio | High compared to average level of normal subjects | | no change, or at least 1% lower | no change, or at least 1% lower |
| AA/Homo-γ-linolenic acid (20:3 n6) ratio | low compared to average level of normal subjects | | no change, or at least 1% increase | no change, or at least 1% increase |
| Acrenic acid (22:4 n6)/ AA ratio | High compared to average level of normal subjects | | no change, or at least 1% lower | no change, or at least 1% lower |
| Ferritin (ng/mL) | | at least 100, 120, 150, 200, 250, 300, 350, 400, or 500 | at least 1% lower | at least 1 to about 95% lower |
| Thioredoxin (ng/mL) | | at least 15, 20, 25, 30, 35, 40, 45, or 50 | at least 1% lower | at least 1 to about 95% lower |
| TNFα (pg/mL) (1.79 or less) | at least 1.5 | at least 1, 1.5, 1.6, 1.7, 1.79, 1.8, 1.9, 2.0, 2.2, 2.5, 3, 3.5, 4, 5, 6, 7 or 10 | at least 1% lower | at least 1 to about 95% lower |

Fig. 5 (continued)

| Item (Typical Normal Values, Units) | Pre-treatment baseline Typical Range(s) | Pre-treatment baseline Observable Ranges or Values | After dosing (effect) values Typical Range(s) | After dosing (effect) values Observable Ranges or Values |
|---|---|---|---|---|
| sTNF-R1 (pg/mL) | | at least 480, 500, 600, 700, 800, 900, 1000, 1100, 1200, 1500, or 2000 | at least 1% lower | at least 1 to about 95% lower |
| sTNF-R2 (pg/mL) | | at least 500, 700, 1000, 1200, 1500, 1700, 2000, 2200, 2500, 2700, or 3000 | at least 1% lower | at least 1 to about 95% lower |
| High Sensitivity C-reactive protein (Hs-CRP, mg/dl) | 0.2 | 0.1 or more, 0.2, 0.3, 0.4, 0.5 or more, ranges of 0.1-1, 0.1-0.8, 0.1-0.5, 0.2-0.5 | at least 1% lower | at least 5 to about 95% lower |
| Connective Tissue Growth Factor (CTGF) | | | at least 1% lower | at least 5 to about 95% lower |
| Serum Soluble CD40 (sCD40, pg/ml) | | 5 pg/ml or more, 10, 20, 30, 50, 70, 100, 120, 150, 170, 200, 220, 250, 300, 350, 400, 450, 500 or more | at least 1% lower | at least 5 to about 95% lower |
| Insulin resistance Index (HOMA-IR) (1.6 or less) | 1.5 or more | 1.6 or less/1.5 or more, 1.6, 2, 2.5, 3, 3.5, 4 | no worsening | no change, at least 1 to about 50% lower |
| Glycated hemoglobin (HbA1c) (4.3-5.8%) | 5.7 or more | a range of 4.3-5.8, 5.7-6.4, 5.8-6.5, 6.5-7.0, 7.0-8.0/5.7 or more, 5.8, 6, 6.5, 7, 7.5, 8, or 8.5 | no worsening | no change, at least 1 to about 50% lower |
| Fasting plasma glucose (FPG) (mg/dl) (less than 100) | 100 or more | less than 100/100 or more, 110, 120, 126, 130, 150, 200, 250, 300/ranges of 100-110, 100-126 | no worsening | no change, or at least 1 to about 50% lower |
| Postprandial plasma glucose (after a meal) | 140 or more | less than 140, 160, 200/140 or more, 170, 180, 200, 250, 300, 350, 400/ranges of 140-200, 140-170, 170-200 | no worsening | no change, or at least 1 to about 50% lower |
| two-hour glucose levels on the 75-g oral glucose tolerance test (mg/dl) (OGTT) | 140-200 | less than 140, 160, 200/140 or more, 170, 180, 200, 250, 300, 350, 400/ranges of 140-200, 140-170, 170-200 | no worsening | no change, or at least 1 to about 50% lower |
| Leptin (ng/ml) | | 5 ng/ml or more, 10, 12, 15, 17, 20, 22, 25, 30, 35, 40 or more | at least 1% lower | at least 1 to about 95% reduction |

Fig. 5
(continued)

| Item (Typical Normal Values, Units) | Pre-treatment baseline | | After dosing (effect) values | |
|---|---|---|---|---|
| | Typical Range(s) | Observable Ranges or Values | Typical Range(s) | Observable Ranges or Values |
| Serum adiponectin (μg/mL) complement factor D | | 5 μg/mL or less, 4.5, 4, 3.5, or 3 μg/mL or less | at least 1% increase | no change, at least 1 to about 99% increase |
| | | | at least 15% lower | at least 1 to about 95% reduction |
| CK18 fragment | | | at least 1% lower | at least 1 to about 95% reduction |
| serum High mobility group box 1 protein (HMGB1) | | | at least 1% lower | at least 1 to about 95% reduction |
| Fas | | | at least 1% lower | at least 1 to about 95% reduction |
| Hyaluronic acid (50 ng/mL or less) | | 25 ng/mL or more, 50, 70, 100, 120, 150, 200, 250, or 300 or more; 200 mL or less, 100, 70, or 50 or less | at least 1% lower | at least 1 to about 95% reduction |
| Type IV collagen (7s domain) (6 ng/mL or less) | | 5 ng/mL or more, 6, 7, 8, 10, 12, 15, or 20 or more; 25 ng/mL or less, 20, 15, 10, or 6 or less | at least 1% lower | at least 1 to about 95% reduction |
| procollagen III peptide 0.3-0.8 U/ml | | 0.2 U/ml or more, 0.3, 0.5, 0.7, 1, 1.2, 1.5, 2, 2.5, 3, 3.5, or 4 or more; 10 or less, 8, 5, 3, 1, or 0.8 or less | at least 1% lower | at least 1 to about 95% reduction |
| PAI-1 (ng/mL) 50 or less | 50 or more | | | |
| | | Items other than serum | | |
| platelet count 150000-400000/μl | 150000-300000 | 400000/μl or less, 300000, 200000/a range of 150000-300000 | no change | no change, at least 1% increase |
| BMI | 18.5-40 | 18.5 or more, 20, 25, 30, 35, 40, or 50 or more; 50 or less, 40, 30, 25, 20 or 18.5 or less; or range of 18.5-25, 25-30, 30-35, 35-40 | no change | no change, at least 1% reduction |

Fig. 5
(continued)

| Proportion of responder (n of responder/n of cases) | All Cases | Placebo | EPA-E 1800mg/day | EPA-E 2700mg/day |
|---|---|---|---|---|
| All Cases | 32.2% (56/174) | 32.7% (18/55) | 32.7% (18/55) | 31.3% (20/64) |
| GGT≦33 | 41.9% (13/31) | 23.1% (3/13) | 45.5% (5/11) | 71.4%* (5/7) |
| GGT>33 | 30.1% (43/143) | 35.7% (15/42) | 29.5% (13/44) | 26.3% (15/57) |

χ square test vs Placebo  *: $p<0.05$

| p value by χ square test vs. Placebo | All Cases | Placebo | EPA-E 1800mg/day | EPA-E 2700mg/day |
|---|---|---|---|---|
| All Cases | - | - | 1.000 | 0.863 |
| GGT≦33 | - | - | 0.247 | 0.035* |
| GGT>33 | - | - | 0.542 | 0.315 |

Fig. 7

| Primary endpoint achieved rate (n of achieved/n of cases) | Placebo | EPA-E 1800mg/day | EPA-E 2700mg/day |
|---|---|---|---|
| GGT=<24,25,26 or 27 | 12.5% (1/8) | 50.0% (2/4) | 60.0%* (3/5) |
| GGT=<28 | 12.5% (1/8) | 40.0% (2/5) | 60.0%* (3/5) |
| GGT=<29 | 12.5% (1/8) | 33.3% (2/6) | 66.7%** (4/6) |
| GGT=<30 | 11.1% (1/9) | 33.3% (2/6) | 66.7%** (4/6) |
| GGT=<31 | 10.0% (1/10) | 28.6% (2/7) | 66.7%** (4/6) |
| GGT=<32 | 16.7% (2/12) | 33.3% (3/9) | 66.7%** (4/6) |
| GGT=<33 | 23.1% (3/13) | 45.5% (5/11) | 71.4%** (5/7) |
| GGT=<34 | 23.1% (3/13) | 41.7% (5/12) | 62.5%* (5/8) |
| GGT=<35 | 23.1% (3/13) | 41.7% (5/12) | 55.5% (5/9) |
| GGT=<40 | 27.8% (5/18) | 38.9% (7/18) | 46.7% (7/15) |
| GGT=<45 | 27.8% (5/18) | 40.9% (9/22) | 33.3% (8/24) |
| GGT=<50 | 28.6% (6/21) | 38.5% (10/26) | 32.1% (9/28) |
| GGT=<55 | 30.4% (7/23) | 35.5% (11/31) | 31.3% (10/32) |
| GGT=<60 | 28.0% (7/25) | 36.4% (12/33) | 31.3% (10/32) |
| GGT male=<30, female=<24 | 11.1% (1/9) | 33.3% (2/6) | 60.0%* (3/5) |

Fig. 8

χ square test   vs. Placebo         *: p<0.10     **: p<0.05

| p value by χ square test vs. Placebo | Placebo | EPA-E 1800mg/day | EPA-E 2700mg/day |
|---|---|---|---|
| GGT=<24,25,26 or 27 | - | 0.157 | 0.071* |
| GGT=<28 | - | 0.252 | 0.071* |
| GGT=<29 | - | 0.347 | 0.036** |
| GGT=<30 | - | 0.292 | 0.025** |
| GGT=<31 | - | 0.323 | 0.018** |
| GGT=<32 | - | 0.375 | 0.034** |
| GGT=<33 | - | 0.247 | 0.035** |
| GGT=<34 | - | 0.319 | 0.071* |
| GGT=<35 | - | 0.319 | 0.119 |
| GGT=<40 | - | 0.480 | 0.261 |
| GGT=<45 | - | 0.386 | 0.700 |
| GGT=<50 | - | 0.477 | 0.788 |
| GGT=<55 | - | 0.697 | 0.949 |
| GGT=<60 | - | 0.502 | 0.790 |
| GGT male=<30, female=<24 | - | 0.292 | 0.052* |

Fig. 8 (continued)

| Change of NAS score mean±SD (n) | Placebo | EPA-E 1800mg/day | EPA-E 2700mg/day |
|---|---|---|---|
| All Cases | 0.927±1.500 (55) | 1.018±1.258 (55) | 0.844±1.573 (64) |
| GGT≦33 | 0.769±1.527 (13) | 1.818±1.029* (11) | 2.286±1.248* (7) |
| GGT>33 | 0.976±1.476 (42) | 0.818±1.230 (44) | 0.667±1.514 (57) |

Student's t test vs Placebo　　*: $p<0.05$

| p value by student's t test vs. Placebo | Placebo | EPA-E 1800mg/day | EPA-E 2700mg/day |
|---|---|---|---|
| All Cases | - | 0.367 | 0.385 |
| GGT≦33 | - | 0.039* | 0.024* |
| GGT>33 | - | 0.298 | 0.159 |

Fig. 9

| EPA/AA ratio at Day365 mean±SD (n) | Placebo | EPA-E 1800mg/day | EPA-E 2700mg/day |
|---|---|---|---|
| All Cases | 0.076±0.080 (46) | 0.311±0.206 (51) | 0.557±0.374 (56) |
| GGT≦33 | 0.124±0.165 (8) | 0.313±0.192 (11) | 1.026±0.488* (7) |
| GGT>33 | 0.077±0.080 (38) | 0.383±0.251 (40) | 0.507±0.326 (49) |

Student's t test vs GGT>33    *: $p<0.05$

| p value by student's t test | Placebo | EPA-E 1800mg/day | EPA-E 2700mg/day |
|---|---|---|---|
| GGT≦33 vs GGT>33 | 0.070 | 0.202 | 0.0004* |

Fig. 10

| Parameter (Baseline) | Group | GGT=<33 | GGT>33 | Stedman [a] | Merck Manual [b] |
|---|---|---|---|---|---|
| GGT (U/L) | Placebo | 24.4±6.4 | 102.9±71.5 | M:2-30 F:1-24 | 8-78 |
| | 1800 | 27.8±4.7 | 98.0±125.2 | | |
| | 2700 | 23.3±6.4 | 95.4±111.9 | | |
| ALP (U/L) | Placebo | 62.8±13.1 | 93.7±38.9 | - | 36-92 |
| | 1800 | 71.1±17.0 | 82.1±24.9 | | |
| | 2700 | 76.3±20.8 | 90.1±25.9 | | |
| Direct Bilirubin (mg/dL) | Placebo | 0.09±0.03 | 0.11±0.05 | 0-0.4 | 0-0.3 |
| | 1800 | 0.11±0.03 | 0.10±0.05 | | |
| | 2700 | 0.11±0.05 | 0.11±0.05 | | |
| ALT (U/L) | Placebo | 47.4±22.9 | 96.0±48.9 | M:13-40 F:10-28 | 0-35 |
| | 1800 | 51.5±28.4 | 94.0±51.9 | | |
| | 2700 | 86.4±79.2 | 81.6±34.8 | | | a) Stedmansonline Laboratory Reference Range Values
b) Merck Manual Appendix II Normal Laboratory Values

Fig. 11

| Parameter (Baseline) | Group | GGT=<33 | GGT>33 | Stedman a) | Merck Manual b) |
|---|---|---|---|---|---|
| AST (U/L) | Placebo | 35.0±12.9 | 69.3±44.2 | 10-59 | 0-35 |
| | 1800 | 36.1±16.1 | 68.6±38.9 | | |
| | 2700 | 66.7±63.7 | 61.1±32.4 | | |
| Albumin (g/dL) | Placebo | 4.52±0.38 | 4.53±0.62 | 3.5-5.2 (>60y:3.2-4.6) | 3.5-5.5 |
| | 1800 | 4.47±0.29 | 4.56±0.27 | | |
| | 2700 | 4.66±0.18 | 4.53±0.29 | | |
| Ferritin (ng/mL) | Placebo | 76.0±51.6 | 253.3±221.4 | M:20-150 F:10-120 | 15-200 |
| | 1800 | 134.7±96.1 | 239.6±264.1 | | |
| | 2700 | 151.3±98.5 | 234.9±159.4 | | |
| CK18 Fragment (U/L) | Placebo | 428.5±229.1 | 928.5±839.5 | - | |
| | 1800 | 357.7±174.4 | 811.5±665.7 | | |
| | 2700 | 546.7±368.4 | 798.0±673.5 | | |

Fig. 11 (continued)

COMPOSITIONS AND METHODS FOR TREATING NON-ALCOHOLIC STEATOHEPATITIS

CROSS-REFERENCE

This application claims the benefit of U.S. Provisional Application No. 61/791,533, filed Mar. 15, 2013; and 61/793,309, filed Mar. 15, 2013; each of which applications is incorporated herein in its entirety by reference.

BACKGROUND

Heavy alcohol use is known to lead to liver complications, including alcoholic hepatitis which is often characterized by fatty liver and inflammation. Alcoholic hepatitis can ultimately lead to cirrhosis of the liver (scarring) and hardening of the liver tissue. However, individuals that do not consume excessive amounts of alcohol can also be found to have liver disease complications. Non-alcoholic fatty liver disease (NAFLD) is understood to encompass a variety of liver diseases, including steatosis (simple fatty liver), non-alcoholic steatohepatitis (NASH) and advanced scarring of the liver (cirrhosis). NASH has traditionally been diagnosed by means of a liver biopsy to characterize the liver histology, particularly with respect to the characteristics of inflammation, fibrosis and steatosis (fat accumulation). NASH then generally refers to clinical findings based upon the liver biopsy of a patient with steatohepatitis, combined with the absence of significant alcohol consumption (Neuschwander-Tetri, B. A. and S. H. Caldwell (2003) Hepatology 37(5): 1202-1209).

In NASH, fat accumulation is seen in varying degrees of inflammation (hepatitis) and may lead to more serious conditions involving scarring (fibrosis). Patients having NASH are also often characterized by abnormal levels of liver enzymes, such as aspartate aminotransferase (AST) and alanine aminotransferase (ALT). Currently, there are few therapies to slow down or alter the course of further disease progression in NASH. Therefore, there remains a need for effective NASH treatments.

SUMMARY OF THE DISCLOSURE

The disclosure provides for a method for treating a fatty liver disorder in a subject in need thereof, comprising selecting a subject having or suspected of having a fatty liver disease or disorder, wherein the subject is non diabetic, pre-diabetic, or mildly diabetic; or has normal or substantially normal biliary tract function; and administering a therapeutically effective amount of a pharmaceutical composition comprising ethyl eicosapentanoate (EPA-E). In some cases EPA-E or EPA present may be at least 40% by weight in total of the fatty acids and their derivatives.

In some embodiments, the present disclosure provides for a method for treating a fatty liver disorder in a subject in need thereof, comprising selecting a subject having or suspected of having a fatty liver disease or disorder, wherein the subject is non diabetic, pre-diabetic, or mildly diabetic; and administering a therapeutically effective amount of a pharmaceutical composition comprising ethyl eicosapentanoate (EPA-E). In some cases the EPA-E present may be at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; and administering a therapeutically effective amount of a pharmaceutical composition comprising ethyl eicosapentanoate (EPA-E).

The disclosure also provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level is normal or substantially normal, and administering a therapeutically effective amount of a pharmaceutical composition comprising ethyl eicosapentanoate (EPA-E).

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; and administering a therapeutically effective amount of a pharmaceutical composition comprising ethyl eicosapentanoate (EPA-E); and administering in step b results in an improvement of serum EPA/AA ratio as compared to a baseline EPA/AA ratio equal to or greater than 0.1, 0.2, 0.3 or 0.4 in the subject. The disclosure also provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level equal to or less than 24, 25, 26, 27, 28, 29, 30, 31, 32, 33, 34, 35, 40, 45, 50, 55, 60 or 78 IU/L, or GGT level equal to or less than 30 or 85 IU/L for men and GGT level equal to or less than 24 or 55 IU/L for women and administering a therapeutically effective amount of a pharmaceutical composition comprising ethyl eicosapentanoate (EPA-E).

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; wherein the subject is not treated with an anti-diabetic agent or has been previously treated with an anti-diabetic agent; and administering a therapeutically effective amount of a pharmaceutical composition comprising ethyl eicosapentanoate (EPA-E), wherein EPA-E present in the composition is at least 40% by weight in total of the fatty acids and their derivatives.

In some embodiments, the disclosure provides for a method for treating a fatty liver disease or disorder in a subject in need thereof, comprising: selecting a subject having or suspected of having a fatty liver disease or disorder, wherein the subject shows a normal or substantially normal biliary function or a serum gamma glutamyl transferase (GGT) level equal to or less than 24, 25, 26, 27, 28, 29, 30, 31, 32, 33, 34, 35, 40, 45, 50, 55, 60 or 78 IU/L, or GGT level equal to or less than 30 or 85 IU/L for men and GGT level equal to or less than 24 or 55 IU/L for women, (a) administering to a subject an effective amount of a pharmaceutical composition comprising ethyl eicosapentanoate (EPA-E); (b) improving the steatosis and lobular inflammation condition of said subject, and no worsening of said fibrosis stage score; and (c) the subject exhibits the following changes in said at least one marker as compared to a baseline pretreatment level of at least 1% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Stearic acid/Palmitic acid ratio, γ-linoleic acid/Linoleic acid ratio, Adrenic acid/ AA ratio, Ferritin, Thioredoxin, TNF α, sTNF-R1, sTNF-R2, Hs-CRP, CTGF, sCD40, Leptin, complement factor D, CK18 fragment, serum HMGB1, Fas, Hyaluronic acid, Type IV collagen (7 s domain), procollagen III peptide or PAI-1; at least 5% increase for EPA or EPA/AA ratio; at least 1% increase for DPA, AA/Homo-γ-linoleic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count or BMI.

In some embodiments, the disclosure provides for a method for treating a fatty liver disease or disorder in a subject in need thereof, comprising: selecting a subject having or suspected of having a fatty liver disease or disorder, wherein the subject's serum HbA1c level is equal to or less than 6.4% or the subject's fasting serum glucose level is equal to or less than 125 mg/dl; administering a therapeutically effective amount of a pharmaceutical composition comprising ethyl eicosapentanoate (EPA-E) in combination with one or more anti-diabetic agents.

In some embodiments, the disclosure provides for a method for treating a fatty liver disease or disorder in a subject in need thereof, comprising: selecting a subject where at least one criteria selected from the group consisting of NAS score, steatosis score, lobular inflammation score, ballooning score and fibrosis stage is indicative of fatty liver disease; and wherein the subject shows a serum gamma glutamyl transferase (GGT) level equal to or less than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women; and administering a therapeutically effective amount of a pharmaceutical composition comprising ethyl eicosapentanoate (EPA-E).

In some embodiments, the disclosure provides for a method for treating a fatty liver disease or disorder in a subject in need thereof, comprising selecting a subject having a: NAS score greater than or equal to 3; or steatosis score equal to or greater than 1; or lobular inflammation score equal to or greater than 1; or ballooning score equal to or greater than 1; or fibrosis score equal to or greater than 1; administering a therapeutically effective amount of a pharmaceutical composition comprising ethyl eicosapentanoate (EPA-E) to the subject; and wherein the subject's serum HbA1c level is equal to or less than 6.4% or ii) the subject's fasting serum glucose level is equal to or less than 125 mg/dl.

In some embodiments, the present disclosure provides for a subject that is non diabetic, pre-diabetic or mildly diabetic. In some aspects of the disclosure, the subject receives no treatment for diabetes or no anti-diabetic agent. In some aspects of the disclosure, the subject receives at least one treatment for diabetes or at least one anti-diabetic agent. In some aspects of the disclosure, the subject receives at least one treatment for diabetes or at least one anti-diabetic agent is administered simultaneously with the pharmaceutical composition.

In some embodiments, the present disclosure provides for an anti-diabetic agent that is selected from the following group: PPARγ agonists, biguanides, protein tyrosine phosphatase-1B (PTP-1B) inhibitors, meglitinides, a glucoside hydrolase inhibitors, insulin secreatagogues, A2 antagonists, insulin and related compounds, non-thiazolidinediones, GSK 3β/GSK 3 inhibitors, dipeptidyl peptidase IV (DP-IV) inhibitors, peptides, sulfonylureas, and nonsulfonylurea secreatagogues.

In some embodiments, the present disclosure provides for a subject who consumes a diabetic diet or a western diet.

In some embodiments, the disclosure provides for a method for treating a fatty liver disease or disorder in a subject in need thereof, comprising: selecting a subject having a: NAS score greater than or equal to 3; or steatosis score equal to or greater than 1; or lobular inflammation score equal to or greater than 1; or ballooning score equal to or greater than 1; or fibrosis score equal to or greater than 1; determining the subject's gamma glutamyl transferase (GGT) serum level; and administering a therapeutically effective amount of a pharmaceutical composition comprising ethyl eicosapentanoate (EPA-E) to the subject, if the subject i) shows a serum gamma glutamyl transferase (GGT) level equal to or less than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women.

In some embodiments, the fatty liver disease or disorder is selected from the group consisting of Non-Alcoholic Fatty Liver Disease (NAFLD) and Non-Alcoholic Steatohepatits (NASH).

In some embodiments, selecting a subject having or suspected of having a fatty liver disease or disorder comprises selecting a subject having a score selected from the group consisting of: a NAS score greater than or equal to 3, a steatosis score equal to or greater than 1, a lobular inflammation score equal to or greater than 1, a ballooning score equal to or greater than 1 and a fibrosis score equal to or greater than 1.

In some embodiments, the disclosure provides for selecting a subject having or suspected of having a fatty liver disease or disorder, further comprising selecting a subject who is overweight.

In some embodiments, the disclosure provides for selecting a subject having or suspected of having a fatty liver disease or disorder, further comprising selecting a subject with a body mass index (BMI) greater than or equal to 25 kg/m$^2$.

In some embodiments, the disclosure provides for selecting a subject having or suspected of having a fatty liver disorder, further comprising selecting a subject with a familial history of fatty liver disease.

In some embodiments, the disclosure provides for selecting a subject having or suspected of having a fatty liver disorder, further comprising selecting a subject with a NAS score greater than or equal to 4.

In some embodiments, the disclosure provides for selecting a subject having or suspected of having a fatty liver disorder comprises selecting a subject with a normal serum direct bilirubin level equal to or less than 0.4, 0.3, 0.2, 0.17 or 0.1.

In some embodiments, a subject is characterized by at least one criteria selected from the group consisting of a baseline ALT value of about 10 to about 300 IU/L; a baseline AST value of about 10 to about 250 IU/L; a baseline steatosis grade of about 2 to 3; and a baseline lobular inflammation grade of about 2 to 3.

In some embodiments, the present disclosure provides for fatty liver disease characterized by the baseline pretreatment level in the subject of at least one criteria selected from the group consisting of ALT in a range of 10 to 300 IU/L, AST in a range of 10 to 250 IU/L, HDL/C in a range of 25 to 55 mg/dl, LDL-C in a range of 100 to 200 mg/dl, triglycerides in a range of 100 to 1000 mg/dl, TC in a range of 170 to 300 mg/dl, High TG and low HDL-C, TG/HDL-C ratio in a range of 3.75 to 10, non-HDL-C in a range of 100 to 250 mg/dl, Free fatty acid in a range of 400 to 1000μ Eq/L, HOMA-IR in a range of 1.5 to 5, HbA1c in a range of 5.7 to 10%, Fasting plasma glucose in a range of 100 to 200 mg/dl, impaired glucose tolerance and metabolic syndrome.

In some embodiments, the present disclosure provides for fatty liver disease characterized by the baseline pretreatment level in the subject of at least one criteria selected from the group consisting of low level of EPA, DPA, DHA, EPA/AA, DHA/AA. DHA/DPA, AA/Homo-γ-linoleic acid: and high level of AA, MUFA, Palmitoleic acid, Oleic acid, Oleic acid/Stearic acid, Palmitoleic acid/Palmitic acid, γ-linoleic acid/Linoleic acid, Adrenic acid/AA compared to each average level in subjects with fatty liver disease.

In some embodiments, the present disclosure provides for administration of EPA-E for about one year, and the subject exhibits at least one improvement selected from the group consisting of a reduced ALT value as compared to said baseline ALT value; a reduced AST value as compared to said baseline AST value; a reduced steatosis grade as compared to said baseline steatosis grade; and a reduced lobular inflammation grade as compared to said baseline lobular inflammation grade.

In some embodiments, the present disclosure provides for a therapeutically effective amount of EPA-E administered to the subject is an amount between about 1800 and about 2700 mg per day.

In some embodiments, the present disclosure provides for a therapeutically effective amount of EPA-E administered to the subject is at least 1800 mg per day.

In some embodiments, the present disclosure provides for a therapeutically effective amount of EPA-E administered to the subject is at least 2700 mg per day.

In some embodiments, the present disclosure provides for the subject further characterized by having at least one condition selected from the group consisting of high triglycerides and low HDL-C, impaired glucose tolerance and metabolic syndrome.

In some embodiments, the present disclosure provides for reduced ALT value at least 5% lower than said baseline ALT value and/or said reduced AST value is at least 5% lower than said baseline AST value.

In some embodiments, the present disclosure provides for determining in a subject prior to treatment a baseline level in serum of at least one member selected from the group consisting of ALT in a range of 10 to 300 IU/L, AST in a range of 10 to 250 IU/L, HDL-C in a range of 25 to 55 mg/dl, LDL-C in a range of 100 to 200 mg/dl, triglycerides in a range of 100 to 1000 mg/dl, TC in a range of 170 to 300 mg/dl, High TG and low HDL-C, TG/HDL-C ratio in a range of 3.75 to 10, non-HDL-C in a range of 100 to 250 mg/dl, Free fatty acid in a range of 400 to 1000μ Eq/L, HOMA-IR in a range of 1.5 to 5, HbA1c in a range of 5.7 to 10%, Fasting plasma glucose in a range of 100 to 200 mg/dl.

In some embodiments, the present disclosure provides for administration of ethyl eicosapentanoate for at least 3 months, said subject exhibits the following changes in said at least one marker as compared to the baseline level of at least 1% reduction for ALT, AST, TG, TG/HDL ratio, Free fatty acid, AA, MUFA, Palmitoleic acid, Oleic acid, Oleic acid/Stearic acid ratio, Palmitoleic acid/Palmitic acid ratio, Adrenic acid/AA ratio, Ferritin, Thioredoxin, TNF α, sTNF-R1, sTNF-R2, Hs-CRP, CRGF, sCD40, Leptin, complement factor D, CK18 fragment, serum HMGB1, Fas, Hyaluronic acid, Type IV collagen (7 s domain), procollagen III peptide or PAI-1; at least 5% increase for EPA or EPA/AA ratio; at least 1% increase for DPA, AA/Homo-γ-linoleic acid ratio or Serum adiponectin; no worsening of ALP, bilirubin, GGT, Albumin, HDL-C, LDL-C, TC, non-HDL-C, HOMA-IR, HbA1c, Glucose, Fasting plasma glucose, postprandial plasma glucose, OGTT, platelet count or BMI.

In some embodiments, the present disclosure provides for improving the steatosis and lobular inflammation condition of said subject, and no worsening of said fibrosis stage score.

In some embodiments, the present disclosure provides for improving the NAS score in said subject (i) to a composite score of 3 and no worsening of said fibrosis stage score, or (ii) by 2 across at least two of the NAS components and no worsening of said fibrosis stage score.

In some embodiments, the present disclosure provides for an improvement in serum EPA/AA ratio as compared to a baseline EPA/AA ratio.

In some embodiments, the present disclosure provides for improvement in serum EPA/AA ratio as compared to a baseline EPA/AA ratio equal to or greater than 0.1, 0.2, 0.3 or 0.4.

In some embodiments, the present disclosure provides for the pharmaceutical composition administered to the subject 1 to 4 times per day.

In some embodiments, the present disclosure provides for the composition present in one or more capsules.

In some embodiments, the present disclosure provides for the composition comprising a self-emulsifying composition comprising 50 to 95% by weight, a ω3 polyunsaturated fatty acids and their pharmaceutically acceptable salts and esters.

In some embodiments, the present disclosure provides for the composition comprising a self-emulsifying composition comprising 50 to 95% by weight, EPA-E and its pharmaceutically acceptable salts and esters.

In some embodiments, the present disclosure provides for the composition comprising a self-emulsifying composition comprising at least 60%, by weight, EPA-E and its pharmaceutically acceptable salts and esters.

In some embodiments, the present disclosure provides for the composition comprising a self-emulsifying composition comprising at least 70%, by weight, EPA-E and its pharmaceutically acceptable salts and esters.

In some embodiments, the present disclosure provides for the composition comprising a self-emulsifying composition comprising at least 80%, by weight, EPA-E and its pharmaceutically acceptable salts and esters.

In some embodiments, the present disclosure provides for the composition comprising a self-emulsifying composition comprising at least 90%, by weight, EPA-E and its pharmaceutically acceptable salts and esters.

In some embodiments, the present disclosure provides for the composition comprising a self-emulsifying composition comprising at least 95%, by weight, EPA-E and its pharmaceutically acceptable salts and esters.

In some embodiments, the present disclosure provides for the composition comprising a self-emulsifying composition comprising at least 96%, by weight, EPA-E and its pharmaceutically acceptable salts and esters.

In some embodiments, the present disclosure provides for the composition comprising, 5 to 50% by weight, an emulsifier having a hydrophilic lipophilic balance of at least 10.

In some embodiments, the present disclosure provides for the composition comprising, 10 to 50% by weight, an emulsifier having a hydrophilic lipophilic balance of at least 10.

In some embodiments, the present disclosure provides for the composition comprising, 20 to 50% by weight, an emulsifier having a hydrophilic lipophilic balance of at least 10.

In some embodiments, the present disclosure provides for the composition comprising, 30 to 50% by weight, an emulsifier having a hydrophilic lipophilic balance of at least 10.

In some embodiments, the present disclosure provides for the composition comprising, 40 to 50% by weight, an emulsifier having a hydrophilic lipophilic balance of at least 10.

In some embodiments, the present disclosure provides for the composition comprising, ethanol content up to 4% by weight in relation to the total content of the compound and the emulsifier.

In some embodiments, the present disclosure provides for the composition not containing ethanol.

In some embodiments, the present disclosure provides for the emulsifier at least one member selected from the group consisting of polyoxyethylene hydrogenated castor oil, polyoxyethylene sorbitan fatty acid ester, polyoxyethylene castor oil, polyethylene glycol fatty acid ester, polyoxyethylene polyoxypropylene glycol, sucrose fatty acid ester, and lecithin.

In some embodiments, the present disclosure provides for the emulsifier as at least one member selected from the group consisting of polyoxyethylene hydrogenated castor oil, polyoxyethylene sorbitan fatty acid ester, polyoxyethylene castor oil, and sucrose fatty acid ester.

In some embodiments, the present disclosure provides for the polyoxyethylene hydrogenated castor oil as at least one member selected from the group consisting of polyoxyethylene (20) hydrogenated castor oil, polyoxyethylene (40) hydrogenated castor oil, polyoxyethylene (50) hydrogenated castor oil, polyoxyethylene (60) hydrogenated castor oil, and polyoxyethylene (100) hydrogenated castor oil.

In some embodiments, the present disclosure provides for the polyoxyethylene sorbitan fatty acid ester as at least one member selected from the group consisting of polyoxyethylene sorbitan monooleate, polyoxyethylene sorbitan tristearate, polyoxyethylene sorbitan monostearate, polyoxyethylene sorbitan monopalmitate, and polyoxyethylene sorbitan monolaurate.

In some embodiments, the present disclosure provides for the sucrose fatty acid ester as at least one member selected from the group consisting of sucrose laurate, sucrose myristate, sucrose palmitate, sucrose stearate, and sucrose oleate.

In some embodiments, the present disclosure provides for the composition as containing a lecithin where lecithin is at least one member selected from the group consisting of soybean lecithin, enzymatically decomposed soybean lecithin, hydrogenated soybean lecithin, and egg yolk lecithin.

In some embodiments, the present disclosure provides the composition as containing a polyhydric alcohol, where it may further comprise propylene glycol or glycerin.

In some embodiments, the present disclosure provides the composition contains at least one member selected from the group consisting of eicosapentaenoic acid, docosahexaenoic acid, and their pharmaceutically acceptable salts and esters.

In some embodiments, the present disclosure provides the composition contains less than 5% eicosapentaenoic acid, and their pharmaceutically acceptable salts and esters.

In some embodiments, the present disclosure provides the composition contains less than 5% docosahexaenoic acid, and their pharmaceutically acceptable salts and esters.

In some embodiments, the present disclosure provides the composition contains ethyl icosapentate and/or ethyl docosahexaenoate.

In some embodiments, the present disclosure provides the composition a total content of the emulsifier having an HLB of at least 10 is 10 to 100 parts by weight in relation to 100 parts by weight of the at least one compound selected from the group consisting of ω3 polyunsaturated fatty acids and their pharmaceutically acceptable salts and esters.

In some embodiments, the present disclosure provides the composition a total content of the emulsifier having an HLB of at least 10 is 10 to 50 parts by weight in relation to 100 parts by weight of the at least one compound selected from the group consisting of EPA-E and its pharmaceutically acceptable salts and esters.

In some embodiments, the present disclosure provides the subject's serum HbA1c level is equal to 6.4%, less than 6.4%, between 5.7% and 6.4%, equal to 5.6% or less than 5.6%

In some embodiments, the present disclosure provides the subject's fasting serum glucose level is equal to 125 mg/dL, less than 125 mg/dL, between 100 mg/dL and 125 mg/dL, equal to 100 mg/dL or less than 100 mg/dL.

In some embodiments, the present disclosure provides the subject's serum HbA1c level is measured using a technique selected from the following group: high-performance liquid chromatography (HPLC); immunoassay; enzymatic assay; colorimetric assay; capillary electrophoresis and boronate affinity chromatography.

In some embodiments, the subject shows a serum gamma glutamyl transferase (GGT) level equal to or less than 24 IU/L.

In some embodiments the subject does not have a condition selected from the following group consisting of alcoholic liver injury, drug-induced liver injury, chronic active hepatitis, cirrhosis, liver cancer, hepatic steatosis and biliary tract disease.

In some embodiments, the present disclosure provides the subject's glucose level is measured using methods selected from the following: FPG, RPG and OGTT.

In some embodiments the subject shows unobstructed or normal excretion of bile, does not suffer from injury in the liver, does not exhibit liver dysfunction, shows normal levels of direct bilirubin, does not possess biliary tract disease or the subject possess biliary tract disease in an early stage.

In some embodiments the subject consumes a diabetic diet or a western diet.

In some embodiments EPA-E is at least 40% by weight in total of the fatty acids and their derivatives in the composition.

In some embodiments, the pharmaceutical composition of the present disclosure may be any EPA-E containing compositions, including commercially available sources such as Lovaza™ (Glaxo SmithKline, FL USA), Omacor™ (Pronova Biopharma ASA, Oslo Norway), Lotriga™ (Takeda Pharmaceutical Co., Ltd., Osaka Japan) or Vascepa™ (Amarin Pharma Inc., NJ USA).

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of a device of this disclosure are set forth with particularity in the appended claims. A better understanding of the features and advantages of this disclosure will be obtained by reference to the following detailed description that sets forth illustrative embodiments, in which the principles of a device of this disclosure are utilized, and the accompanying drawings.

FIG. 1 is a table representing the proportion of responders to EPA-E treatment (NAS Score ≤3 or improvement of ≥2 across at least 2 of NAS components) in a group of non diabetic (including pre-diabetic) and mild diabetic patients.

FIG. 2 is a table representing further characterization of the patients in FIG. 1. The table reflects the proportion of responders to EPA-E treatment (NAS Score ≤3 or improvement of ≥2 across at least 2 of NAS components) in a sub-group of non diabetic (including pre-diabetic) patients with HbA1c levels=<6.4.

FIG. 3 is a table representing further characterization of the patients in FIG. 1. The table reflects the proportion of responders to EPA-E treatment (NAS Score ≤3 or improvement of ≥2 across at least 2 of NAS components) in a sub-group of non diabetic (including pre-diabetic) and diabetic patients with fasting glucose levels=<125 mg/dL.

FIG. 4 is a table representing further characterization of the patients in FIG. 1. The chart reflects the proportion of responders to EPA-E treatment (NAS Score ≤3 or improvement of ≥2 across at least 2 of NAS components) in a sub-group of non diabetic (including pre-diabetic) and diabetic patients with fasting glucose levels=<125 mg/dL and HbA1c levels=<6.4.

FIG. 5 is a table of possible criteria for the evaluation of NASH for baseline scores before treatment, or after treatment.

FIG. 7 is a table representing the proportion of responders to EPA-E treatment (NAS Score ≤3 or improvement of ≥2 across at least 2 of NAS components) in a group of patients found to have γ-Glutamyl Transferase (GGT) levels ≤33 IU/L.

FIG. 8 is a table of γ-Glutamyl Transferase (GGT) levels in the patients shown in FIG. 7 at the completion of the study.

FIG. 9 is a table representing further characterization of the patients shown in FIG. 7. The table reflects the improvement in NAS score of patients with γ-Glutamyl Transferase (GGT) levels ≤33 IU/L.

FIG. 10 is a table representing further characterization of the patients shown in FIG. 7. The table reflects the improvement of serum EPA/AA ratio on Day 365 of patients with γ-Glutamyl Transferase (GGT) levels ≤33 IU/L.

FIG. 11 is a table corresponding reference values for parameters of liver function in patients with γ-Glutamyl Transferase (GGT) levels ≤33 IU/L and patients with γ-Glutamyl Transferase (GGT) levels ≥33 IU/L.

I. TERMINOLOGY

Figure 6:
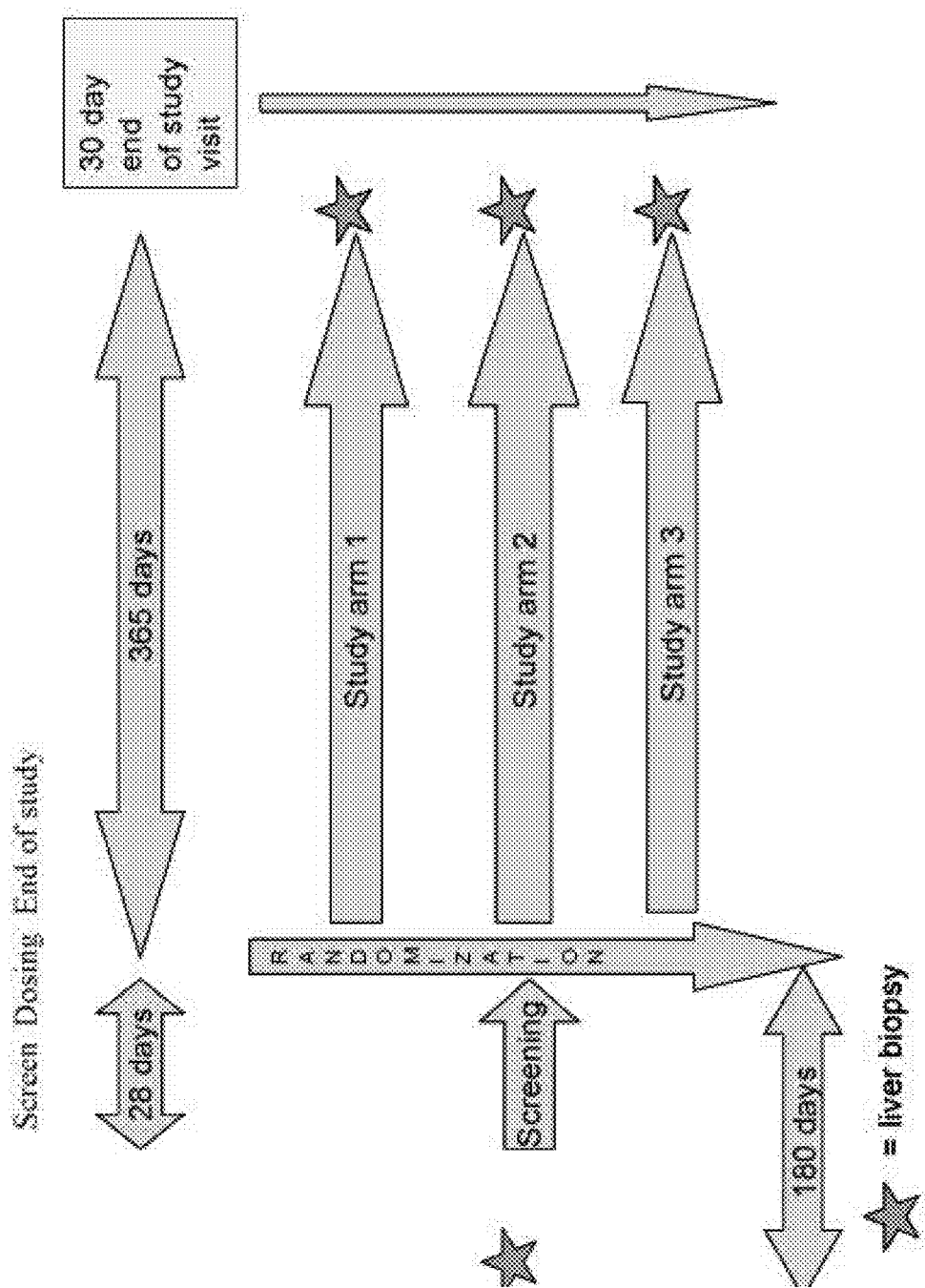
FIG. 6 is a schematic of the experimental screen dosing at the end of a clinical trial study as described herein.

The terminology of the present disclosure is for the purpose of describing particular embodiments only and is not intended to be limiting of compositions, methods and devices of this disclosure.

The terms "methods of treating" mean amelioration, prevention or relief from the symptoms and/or effects associated with NAFLD-associated disorders. As used herein, reference to "treatment" of a patient is intended to include prophylaxis.

As used herein, a "therapeutically effective amount" of a drug or pharmaceutical composition or formulation, or agent, described herein is an amount of a drug or agent that, when administered to a subject with a disease or condition, will have the intended therapeutic effect, e.g., alleviation, amelioration, palliation or elimination of one or more manifestations of the disease or condition in the subject. The full therapeutic effect does not necessarily occur by administration of one dose and may occur only after administration of a series of doses. Thus, a therapeutically effective amount may be administered in one or more administrations.

A "subject" or "patient" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

The term "pre-diabetic" is the condition wherein an individual is pre-disposed to the development of type 2 diabetes. Pre-diabetes extends the definition of impaired glucose tolerance to include individuals with a fasting blood glucose within the high normal range ≥100 mg/dL (J. B. Meigs, et al. Diabetes 2003; 52:1475-1484) and fasting hyperinsulinemia (elevated plasma insulin concentration), fasting serum glucose levels between 100 mg/dL and 125 mg/dL, or HbA1c levels between 5.7% and 6.4%. The scientific and medical basis for identifying pre-diabetes as a serious health threat is laid out in a Position Statement entitled "The Prevention or Delay of Type 2 Diabetes" issued jointly by the American Diabetes Association and the National Institute of Diabetes and Digestive and Kidney Diseases (Diabetes Care 2002; 25:742-749). Pre-diabetic may be include in non-diabetic as provided by this disclosure.

The term "mildly-diabetic" is the condition wherein an individual in early progression of the development of type 2 diabetes. Diabetes extends the definition of impaired glucose tolerance to include individuals with a fasting blood glucose within the high normal range ≥126 mg/dL and/or HbA1c levels ≥6.5%. Mild-diabetes is diabetes who receives no treatment for diabetes, no ant-diabetic agents or only one anti-diabetic agent.

The term "non-diabetic" is the condition wherein an individual does not present impaired glucose tolerance and includes individuals with a fasting blood glucose within the normal range less than 100 mg/dL or HbA1c levels equal to or less than 5.6%.

The term "HbA1c" refers to the product of a non-enzymatic glycation of the haemoglobin B chain. Its determination is well known to one skilled in the art. In monitoring the treatment of diabetes mellitus the HbA1c value is of exceptional importance. As its production depends essentially on the blood sugar level and the life of the erythrocytes, the HbA1c in the sense of a "blood sugar memory" reflects the average blood sugar levels of the preceding 4-6 weeks.

The term "biliary tract function" is any anatomical, physiological or biochemical function provided by the biliary tract in the body. The biliary tract is the common anatomical term for a duct that transports bile, secreted by the liver, to the small intestine (duodenum). As provided by this disclosure, biliary traction function may also include secretion of bile. Additionally, biliary tract function may also include the excretion of bilirubin, a byproduct of red blood cells recycled by the liver.

The term "normal" or "substantially normal" as applied to biliary tract function refers to unobstructed or otherwise functioning transport of bile. Abnormal biliary tract function or biliary disease, used interchangeably herein, may include but is not limited to abnormal or elevated levels of markers associated with biliary disease, obstruction of the bial duct, decreased secretion of bile or bilirubin, failure to secrete bile or bilirubin, abnormal pressure in the biliary duct, gallstones or cirrhosis of the liver as a result thereof.

The term "GGT" refers to γ-glutamyl transferase enzyme or gamma-glutamyl transpeptidase (also γ-glutamyltransferase, GGT, GGTP, gamma-GT). This enzyme catalyzes the transfer of gamma-glutamyl functional groups of glutathione which is a strong anti-oxidant. It is found in many tissues, the most notable one being the liver, and has significance in medicine as a diagnostic marker. Other lines of evidence indicate that GGT can also exert a prooxidant role, A digested product of glutathione "Cys-Gly", in conjunction with metal ions, will produce active oxygen. Therefore, oxidation stress may increase when GGT level remains high.

The term "GGT test" refers to a common liver function test to test the activity levels of GGT. Blood test results for GGT suggest that the normal value is 8-78 IU/L (Merck Manual Appendix II, 2001, Merck Sharp & Dohme Corp., NJ USA), for men is 2-30 IU/L (Duh S H., Laboratory Reference Range Values, 2005, StedmansOnline, Lippincott Williams & Wilkins, PA USA) or 15-85 IU/L (*General Laboratory Manual*. Department of Pathology, Hackensack University Medical Centre. 2010. p. 117), whereas for women it is 1-24 IU/L (Laboratory Reference Range Values) or 5-55 IU/L (*General Laboratory Manual*. Department of Pathology, Hackensack University Medical Centre. 2010. p. 117).

The term "liver injury" or "liver disease" or "liver dysfunction" may be used interchangeably and refer to any injury of the liver, including but not limited to hardening of the liver, scarring of the liver, decreased or abnormal biliary tract function, abnormal liver enzyme activity, cirrhosis of the liver, abnormal physiology as determined by common diagnostic methods include but not limited to ultrasound, or biopsy/histopathology, necrosis of the liver and the like.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising".

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. The term "about" as used herein refers to a range that is 15% plus or minus from a stated numerical value within the context of the particular usage. For example, about 10 would include a range from 8.5 to 11.5. The term "about" also accounts for typical error or imprecision in measurement of values.

II. TREATMENT INDICATIONS

The methods and compositions of the present disclosure are useful for the treatment of subjects having fatty liver related disorders and are known, or suspected to be, non-diabetic, pre-diabetic, or mildly diabetic, by administration of an effective amount of ethyl eicosapentaenoic acid (EPA-E). The methods and compositions of the present disclosure are also useful for the treatment of subjects having fatty liver related disorders and are known to have or suspected of having normal or substantially normal biliary tract function, by administration of an effective amount of ethyl eicosapentaenoic acid (EPA-E).

a. Fatty Liver Disorders

This disclosure provides compositions and methods for treating fatty liver disorders which may include but are not limited to non-alcoholic steatohepatitis (NASH), non-alcoholic associated fatty liver disease, secondary NAFLD, steatosis, progressive fibrosis, liver failure and cirrhosis. As used herein, secondary NAFLD may refer to NAFLD or similar symptoms that result from the use of one or more of the following medications: amiodarone, antiviral drugs such as nucleoside analogues, aspirin or NSAIDs, corticosteroids, methotrexate, nifedipine, perhexyline, tamoxifen, tetracycline, and valproic acid. The term fatty liver disorder, NASH, as described herein, may be referred to and used interchangeably as NASH herein.

B. Diabetes

This disclosure also provides compositions and methods for treating NASH subjects who may also be or suspected to be non-diabetic, pre-diabetic, or mildly diabetic. Diabetes mellitus, commonly called diabetes, refers to a disease process derived from multiple causative factors and characterized by elevated levels of plasma glucose, referred to as hyperglycemia. There are two major forms of diabetes: Type 1 diabetes (also referred to as insulin-dependent diabetes or IDDM) and Type 2 diabetes (also referred to as noninsulin dependent diabetes or NIDDM). Type 1 diabetes is the result of an absolute deficiency of insulin, the hormone that regulates glucose utilization. Type 1 diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies. Type 2 diabetes is a disease characterized by insulin resistance accompanied by relative, rather than absolute, insulin deficiency. Premature development of atherosclerosis and increased rate of cardiovascular and peripheral vascular diseases are characteristic features of patients with diabetes.

Subjects referred herein as "diabetic" may have diabetes or associated conditions. Diabetes, may include but is not limited to Type 1 diabetes, Type 2 diabetes, gestational diabetes mellitus (GDM), maturity onset of diabetes of the young (MODY), pancreatitis, polycystic ovarian disease, impaired glucose tolerance, insulin resistance, hyperglycemia, hyperinsulinemia, elevated blood levels of fatty acids or glycerol, obesity, Syndrome X, dysmetabolic syndrome and related diseases, diabetic complications (including retinopathy, neuropathy, nephropathy) and sexual dysfunction.

The conditions, diseases, and maladies collectively referenced to as "Syndrome X" or Dysmetabolic Syndrome (as detailed in Johanson, J. Clin. Endocrinol. Metab., 1997, 82, 727-734, and other publications) include hyperglycemia and/or prediabetic insulin resistance syndrome, and is characterized by an initial insulin resistant state generating hyperinsulinemia, dyslipidemia, and impaired glucose tolerance, which can progress to Type II diabetes, characterized by hyperglycemia, which can progress to diabetic complications or NAFLD.

C. Biliary Tract Function

This disclosure also provides compositions and methods for treating NASH subjects who are known to have or suspected of having normal or substantially normal biliary tract function. As herein described, biliary tract function generally relates to any function of the biliary of tract in the body, including anatomical, physiological and biochemical function. The primary function of the biliary tract is the transport of bile, secreted by the liver, to the small intestine. As provided by this disclosure, biliary tract function may also include the secretion of bile.

Bile or gall, is a dark green, or yellowish fluid that aids in the process of the digestion of lipids in the small intestine. Bile is stored in the gallbladder and upon eating, is discharged into the duodenum. Bile may comprise water, bile salts, mucus and pigments, fats and inorganic salts.

Bile may act a surfactant, aiding in emulsifying the fats in food. Bile salts may be amphopathic, wherein salts contain both hydrophilic and hydrophobic elements. Bile may form micelles around hydrophobic molecules, such as fats and fatty acids, wherein the hydrophobic sides orient toward the hydrophobic molecule with the hydrophilic sides facing outward. Bile is also used for the excretion of bilirubin, a byproduct of red blood cells recycled by the liver. It is well known that bile enhances forming micelles and an absorption of fatty acids at small intestine.

D. Evaluation Criteria for Subjects with NASH

Generally, any suitable method or combination of methods may be used in evaluating NASH in a subject. In terms of physical symptoms, NASH is generally asymptomatic until severe liver impairment occurs. Patients may generally feel well in the early stages and only begin to have symptoms, such as fatigue, weight loss, and weakness once the disease is more advanced or cirrhosis develops. The progression of NASH may take years, or even decades. The process can stop and, in some cases, reverse on its own without specific therapy. In some cases, NASH may slowly worsen, causing scarring or "fibrosis" to appear and accumulate in the liver. As fibrosis worsens, cirrhosis develops; the liver becomes seriously scarred, hardened, and unable to function normally. Not every person with NASH develops cirrhosis, but once serious scarring or cirrhosis is present, few treatments can halt the progression. A person with cirrhosis experiences fluid retention, muscle wasting, bleeding from the intestines, and liver failure. These physical symptoms in the late stages of the disorder may be used to determine the presence or absence of NASH in a subject.

i. Biopsy

Due to the asymptomatic nature of the disorder, particularly in early stages of the disease, one or more technique and methods may be used to assess the absence or presence of NASH in a subject. In some cases, a biopsy is performed on the liver, whereby a needle is inserted through the skin to remove a small piece of the liver. NASH is diagnosed when examination of the tissue with a microscope shows fat along with inflammation and damage to liver cells. If the tissue shows fat without inflammation and damage, simple fatty liver or NAFLD is diagnosed. In some cases, a biopsy may also indicate the presence or absence of scar tissue that has developed in the liver. Currently, no blood tests or scans can reliably provide this information.

ii. Blood Tests and Biomarkers

While there are no single laboratory tests for NASH, various abnormal levels of liver enzymes, biomarkers and other biological blood components may be used in aiding diagnosis of the disorder. For example, in some cases, elevated serum aminotransferase may indicate NASH. In some cases measuring the level of a plurality of suitable biomarkers in a sample derived from the subject may be used. In some cases such as adipocytokine, apoptosis markers, and/or cell death markers, may be analyzed and compared to reference levels to aid in diagnosis of NASH.

In some cases subjects treated for NASH according to the present disclosure can also be evaluated for baseline scores of the following criteria before treatment, and evaluated after treatment for possible changes in those criteria. The evaluated criteria can comprise one or more of the following criteria set forth in FIG. 5.

iii. NAS Score

In some cases, patients or subjects treated for NASH according to the present disclosure can also be evaluated using a combination of standardized histologic scores, as known in the art. Due to significant inter-observer variance in the clinical diagnosis of NASH, and the severity of the disorder at given time, a composite score of histologic features using a standardized NASH scoring system has been implemented and can be used to provide a measurement of NASH in a subject. This combined measurement is known as the non-alcoholic fatty liver disease activity score (NAS).

In some cases the NAS score may be determined for a subject prior to initiation of treatment in order to provide a baseline level or score for the criteria as well as evaluation after the dosing regimen to evaluate any improvement in the criteria. In other cases, a NAS score may be determined for a subject undergoing treatment. In some cases, a NAS score and comparison of NAS scores over time may be used in assess disease progression of NASH.

The non-alcoholic fatty liver disease activity score (NAS) is defined as the unweighted sum of the values for steatosis (ranging from 0-3), lobular inflammation (ranging from 0-3) and ballooning (ranging from 0-2), thereby providing a range of NAS score of from 0 to 8. (See Kleinen et al., Design and Validation of a Histological Scoring System for Nonalcoholic Fatty Liver Disease, Hepatology, Vol. 41, No. 6, 2005, pp. 1313-1321) Patients treated for NASH according to the present disclosure can show a NAS score prior to treatment of ≥4, with a minimum score of 1 each for steatosis and lobular inflammation plus either ballooning or at least 1 a sinusoidal fibrosis and a finding of possible or definite steatohepatitis. After dosing/treatment, such as for one year, patients can show a composite NAS score of ≤3, ≤2 or ≤1, together with no worsening in fibrosis. Alternatively, patients can show an improvement in NAS by a value of ≥2 across at least two of the NAS components, together with no worsening in fibrosis. Alternatively, patients can show an improvement in NAS score by ≥3, 4, 5, 6, 7 or 8.

iv. Steatosis

Steatosis is broadly understood to describe a process involving the abnormal accumulation of lipids within the liver, which inhibits normal liver function. Liver biopsy enables analysis and scoring of steatosis in a patient, with scores ranging from 0-3. Patients treated for NASH according to the present disclosure can have a steatosis score of 1, 2 or 3, such as between about 2 and about 3. After treatment, it is desired for patients to exhibit no worsening of steatosis, alternatively a reduction of at least 1 in the steatosis score, or a reduction of 2 or 3 in the steatosis score. Steatosis is traditionally graded with a score of 1 indicating the presence of fat droplets in less than 33% of hepatocytes, a score of 2 indicating fat droplets observed in 33-66% of hepatocytes, and a score of 3 indicating observation of fat droplets in greater than 66% of hepatocytes. (See Kleinen et al., Design and Validation of a Histological Scoring System for Nonalcoholic Fatty Liver Disease, Hepatology, Vol. 41, No. 6, 2005, pp. 1313-1321)

v. Lobular Inflammation

Lobular inflammation is also evaluated upon liver biopsy and scored with values of 0-3. (See Kleinen et al., Design and Validation of a Histological Scoring System for Nonalcoholic Fatty Liver Disease, Hepatology, Vol. 41, No. 6, 2005, pp. 1313-1321 Table 1) Patients to be treated for NASH can have lobular inflammation scores of 1, 2 or 3, alternatively ranging between 1 and 2 or 2 and 3. After treatment, patients can have a reduction in lobular inflammation score of at least 1, alternatively a reduction of 2 or 3 in lobular inflammation score, and at least no worsening of the lobular inflammation score.

vi. Ballooning

Ballooning of hepatocytes is generally scored with values of 0-2, (See Kleinen et al., Design and Validation of a Histological Scoring System for Nonalcoholic Fatty Liver Disease, Hepatology, Vol. 41, No. 6, 2005, pp. 1313-1321 Table 1), and patients treated for NASH according to the present disclosure can have ballooning scores of 0-2, including specific values of 1 or 2, and alternatively a score ranging from 1 to 2. After treatment, patients can show at least no worsening of the ballooning score, alternatively a reduction of at least one value lower in the ballooning score, and alternatively a reduction of two in the value of the ballooning score.

vii. Fibrosis Stage

Fibrosis is also evaluated upon liver biopsy and scored with values of 0-4, the scores being defined as: 0 represents no fibrosis, 1 represents perisinusoidal or periportal fibrosis, 1a represents mild, zone 3, perisinusoidal fibrosis; 1b represents moderate zone 3, perisinusoidal fibrosis; 1c represents portal/periortal fibrosis; 2 represents perisinusoidal and portal/periportal fibrosis; 3 represents bridging fibrosis; and 4 represents cirrhosis. (See Kleinen et al., Design and Validation of a Histological Scoring System for Nonalcoholic Fatty Liver Disease, Hepatology, Vol. 41, No. 6, 2005, pp. 1313-1321) Patients treated according to the present disclosure can have a fibrosis stage score of 0-3, including 0, 1, 1a, 1b, 1c, 2 or 3, and can have a fibrosis stage score of at least 1a. After treatment, patients can have a fibrosis stage score that is at least no worse than the baseline score, and alternatively can have a reduction in the fibrosis stage score of at least one level, alternatively at least two or three levels.

E. Evaluation Criteria of Diabetes in NASH Subjects

As described herein, the methods and compositions of the present disclosure are useful for the treatment of subjects having fatty liver related disorders and are known, or suspected to be, non-diabetic, pre-diabetic, or mildly diabetic, by administration of an effective amount of ethyl eicosapentaenoic acid (EPA-E). The presence of absence of non diabetes, pre-diabetes, or mild diabetes may be determined in a subject using any suitable methods known in the art. Generally, preferred tests for diabetes in NASH patients may be characterized in two groups: serum glucose-based tests and glycated proteins. Serum glucose-based tests may include but are not limited to tests such as fasting plasma glucose (FPG), random plasma glucose (RPG), and the oral glucose tolerance test (OGTT). Tests of glycated proteins may include but are not limited to tests that measure proteins such as HbA1c. In some cases, one or more tests may be used to determine the presence or absence of non diabetes, pre-diabetes, or mild diabetes. In some cases a combination of tests may be used to assess diabetes in NASH subjects.

i. Fasting Plasma Glucose (FPG)

The FPG test is a simple plasma glucose measurement obtained after at least 8 hours of fasting (usually an overnight fast). This test may be used for screening and diagnosis of diabetes in NASH subjects due to ease, expense and risk factors. FPG is the ADA test of choice for diagnosis of both pre-diabetes and diabetes. When compared directly, FPG has better intra-individual reproducibility than 2-hour post-load plasma glucose, with intra-individual coefficients of variation of 6.4-11.4% for FPG versus 14.3-16.7% for 2-hour plasma glucose.

FPG may be a reliable predictor of diabetes complications at the current threshold for diagnosis, and studies examining FPG have underlined much of the current knowledge about the pathology of diabetes. However, as known in the art the threshold for pre-diabetes and its relationship to complications may vary across individuals or populations of individuals. General ranges for FPG for assessing non diabetes, pre-diabetes, or mild diabetes are described herein.

ii. Causal Plasma Glucose (RPG)

RPG (or "casual" plasma glucose) measurements may be easily obtained from NASH subjects, do not require fasting, and are frequently included in a basic metabolic panel ordered for other purposes. RPG tests may be determine diabetes, wherein a commonly accepted RPG threshold is ≥200 mg/dl, along with symptoms of polyuria, polydipsia, and unexplained weight loss to indicate a second test for confirmation of diagnosis. An RPG of 140-199 mg/dl is suggestive of pre-diabetes. Based on diagnosis by OGTT, an RPG ≥200 mg/dl is insensitive but has a specificity approaching 100%.

Impairing the overall utility of the RPG as a testing tool is the absence of data comparing it directly to rates of diabetes-specific complications. For this reason, use of the RPG test may be used for rapid, any-time testing with high specificity in symptomatic NASH subjects.

iii. Oral Glucose Tolerance Test (OGTT)

Alternative tests for glucose also may include oral glucose tolerance testing. In some cases it is the preferred test for diabetes diagnosis. Regarding the diagnosis of diabetes, OGTT identifies about 2% more individuals than does FPG, OGTT has poor reproducibility compared to other glucose-based tests such as A1C.

HbA1c testing is known in the art as a standardized measure for diabetes diagnosis that is now broadly used for both research and clinical purposes and may used to determine the presence of absence of non diabetes, pre-diabetes, or mild diabetes in NASH subjects. Its major practical advantages are that it can be obtained in both fasting and nonfasting states, and it represents average glucose control over a period of months rather than a single point value. The ADA recommends this test a first-line test for screening and diagnosis. At approximately the same time, the International Expert Committee released the formal recommendation of an HbA1c level ≥6.5% for diabetes diagnosis.

HbA1c level may be measured using any suitable biochemical techniques. These may include but are not limited to high-performance liquid chromatography (HPLC); immunoassay; enzymatic assay; colorimetric assay; capillary electrophoresis and boronate affinity chromatography.

As with the glucose-based tests, there is no finite threshold of HbA1c at which normality ends and diabetes begins. The International Expert Committee has elected to recommend a cut point for diabetes diagnosis that emphasizes specificity, commenting that this "balanced the stigma and cost of mistakenly identifying individuals as diabetic against the minimal clinical consequences of delaying the diagnosis in someone with an HbA1c level <6.5%.

iv. General Thresholds for Evaluating Diabetes

The tests recommended for screening are the same as those for making the diagnosis, with the result that a positive screen is equivalent to a diagnosis of mild diabetes, pre-diabetes or diabetes. The term "pre-diabetes" has been assigned to those considered to be at higher risk for developing diabetes. In some cases, pre-diabetes is diagnosed by having one or both of the following: 1) an FPG of 100-125 mg/dl, which is also referred to as impaired fasting glucose (IFG) or 2) a 2-hour, 75-g OGTT, with 2-hour plasma glucose levels of 140-199 mg/dl, which is also described as IGT. To get a diagnosis of diabetes, patients must satisfy one of the following criteria: 1) symptoms of diabetes (polyuria, polydipsia, and unexplained weight loss) AND an RPG ≥200 mg/dl, 2) an FPG ≥126 mg/dl, or 3) a 2-hour plasma glucose level ≥200 mg/dl during a 75-g OGTT. Additional diagnostic criteria of an HbA1c result ≥6.5% may also indicate pre-diabetes or mild diabetes. Subjects having mild diabetes may have levels at or about threshold levels as described herein.

As already described herein, the term "pre-diabetic" in the present disclosure extends the definition of impaired glucose tolerance to include individuals with a fasting blood glucose within the high normal range 100 mg/dL (J. B. Meigs, et al. Diabetes 2003; 52:1475-1484) and fasting hyperinsulinemia (elevated plasma insulin concentration), or HbA1c levels between 5.7% and 6.4%.

The term "mildly-diabetic" extends the definition of impaired glucose tolerance to include individuals with a fasting blood glucose within the high normal range 126 mg/dL and/or HbA1c levels ≥6.5% and who receives no treatment for diabetes, no ant-diabetic agents or only one anti-diabetic agent.

The term "non-diabetic" is the condition wherein an individual does not present impaired glucose tolerance and includes individuals with a fasting blood glucose within the normal range less than 100 mg/dL or HbA1c levels less equal to or less than 5.6%.

In some instances, wherein a NASH subject may be pre-diabetic or mildly diabetic, the NASH subject may undergo treatment or receive an anti diabetic agent. In some cases a NASH subject may have a western diet, which may comprise foods heavy in carbohydrates and fats. In other cases, a NASH subject may adopt a diabetic diet, which may comprise a lower carbohydrate diet. In some cases, a NASH subject may receive one or anti-diabetic agents alone or in combination with the pharmaceutical compositions of this disclosure. In some cases, the anti-diabetic may be administered simultaneously as the pharmaceutical composition. In some cases, the pharmaceutical compositions are administered after a NASH subject receives one or more anti-diabetic agents.

v. Anti-Diabetic Agents

In some cases as NASH a subject may be receive one or more anti diabetic agents which may include: PPARγ agonists such as glitazones (e.g., WAY-120,744, AD 5075, balaglitazone, ciglitazone, darglitazone (CP-86325, Pfizer), englitazone (CP-68722, Pfizer), isaglitazone (MIT/J&J), MCC-555 (Mitsibishi disclosed in U.S. Pat. No. 5,594,016), pioglitazone (such as such as Actos™ pioglitazone; Takeda), rosiglitazone (Avandia™; Smith Kline Beecham), rosiglitazone maleate, troglitazone (Rezulin®, disclosed in U.S. Pat. No. 4,572,912), rivoglitazone (CS-011, Sankyo), GL-262570 (Glaxo Welcome), BRL49653 (disclosed in WO98/05331), CLX-0921, 5-BTZD, GW-0207, LG-100641, JJT-501 (JPNT/P&U), L-895645 (Merck), R 119702 (Sankyo/Pfizer), NN-2344 (Dr. Reddy/NN), YM-440 (Yamanouchi), LY-300512, LY-519818, R483 (Roche), T131 (Tularik) and the like.

In some cases an anti diabetic agent may comprise biguanides such as metformin hydrochloride (N,N-dimethylimidodicarbonimidic diamide hydrochloride, such as Glucophage™ Bristol-Myers Squibb); metformin hydrochloride with glyburide, such as Glucovance™, Bristol-Myers Squibb); buformin (Imidodicarbonimidic diamide, N-butyl-); etoformine (1-Butyl-2-ethylbiguanide, Schering A. G.); other metformin salt forms (including where the salt is chosen from the group of, acetate, benzoate, citrate, ftimarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octanoate, decanoate, hexadecanoate, octodecanoate, benzenesulphonate, trimethoxybenzoate, paratoluenesulphonate, adamantanecarboxylate, glycoxylate, glutamate, pyrrolidonecarboxylate, naphthalenesulphonate, 1-glucosephosphate, nitrate, sulphite, dithionate and phosphate), and phenformin; bile acid sequestrants that include, but are not limited to, cholestyramine (i.e., QUESTRAN®, QUESTRAN LIGHT®, CHOLYBAR®, CA registry no. 11041-12-6), colesevelam (i.e., WELCHOL®, CA registry nos. 182815-43-6 and 182815-44-7), ursodeoxycholic acid (i.e. CA registry no. 128-13-2), colestipol (i.e., COLESTID®, CA registry nos. 50925-79-6 and 37296-80-3), sevelamer, dialkylaminoalkyl derivatives of a cross-linked dextran, LOCHOLEST®, DEAE-Sephadex (SECHOLEX®, POLIDEXIDEL®), water soluble derivatives such as 3,3-ioene, N-(cycloalkyl)alkylamines and poliglusam, insoluble quaternized polystyrenes, saponins and mixtures thereof, those bile acid sequestrants disclosed in WO97/11345, WO98/57652, U.S. Pat. No. 3,692,895, and U.S. Pat. No. 5,703,188, including pharmaceutically acceptable salts or mixtures thereof. Suitable inorganic cholesterol sequestrants include bismuth salicylate plus montmorillonite clay, aluminum hydroxide and calcium carbonate antacids.

In some cases an anti diabetic agent may comprise protein tyrosine phosphatase-1B (PTP-1B) inhibitors, such as A-401,674, KR 61639, OC-060062, OC-83839, OC-297962, MC52445, MC52453, ISIS 113715, and those disclosed in WO99/585521, WO99/58518, WO99/58522, WO99/61435, WO03/032916, WO03/032982, WO03/041729, WO03/055883, WO02/26707, WO02/26743, JP2002114768, and pharmaceutically acceptable salts and esters thereof; sulfonylureas such as acetohexamide (e.g., Dymelor, Eli Lilly), carbutamide, chlorpropamide (e.g., Diabinese®, Pfizer), gliamilide (Pfizer), gliclazide (e.g., Diamcron, Servier Canada Inc), glimepiride (e.g., disclosed in U.S. Pat. No. 4,379,785, such as Amaryl™, Aventis), glipentide, glipizide (e.g., Glucotrol or Glucotrol XL Extended Release, Pfizer), gliquidone, glisolamide, glyburide/glibenclamide (e.g., Micronase or Glynase Prestab, Pharmacia & Upjohn and Diabeta, Aventis), tolazamide (e.g., Tolinase), and tolbutamide (e.g., Orinase), and pharmaceutically acceptable salts and esters thereof.

In some cases an anti diabetic agent may comprise meglitinides such as repaglinide (e.g., Pranidin®, Novo Nordisk), KAD1229 (PF/Kissei), and nateglinide (e.g., Starlix®, Novartis), and pharmaceutically acceptable salts and esters thereof;

In some cases an anti diabetic agent may comprise a glucoside hydrolase inhibitors (or glucoside inhibitors) such as acarbose (e.g., Precose™, Bayer disclosed in U.S. Pat. No. 4,904,769), miglitol (such as Glyset™, Pharmacia & Upjohn disclosed in U.S. Pat. No. 4,639,436), camiglibose (Methyl 6-deoxy-6-[(2R,3R,4R,5S)-3,4,5-trihydroxy-2-(hydroxymethyl)piperidino]-alpha-D-glucopyranoside, Marion Merrell Dow), voglibose (Takeda), adiposine, emiglitate, pradimicin-Q, salbostatin, CKD-711, MDL-25,637, MDL-73,945, and MOR 14, and the like.

In some cases an anti diabetic agent may comprise insulin secreatagogues such as linogliride, A-4166, forskilin, dibutyrl cAMP, isobutylmethylxanthine (IBMX), and pharmaceutically acceptable salts and esters thereof, fatty acid oxidation inhibitors, such as clomoxir, and etomoxir, and pharmaceutically acceptable salts and esters thereof.

In some cases an anti diabetic agent may comprise A2 antagonists, such as midaglizole, isaglidole, deriglidole, idazoxan, earoxan, and fluparoxan, and pharmaceutically acceptable salts and esters thereof.

In some cases an anti diabetic agent may comprise insulin and related compounds (e.g., insulin mimetics) such as biota, LP-100, novarapid, insulin detemir, insulin lispro, insulin glargine, insulin zinc suspension (lente and ultralente), Lys-Pro insulin, GLP-1 (1-36) amide, GLP-1 (73-7) (insulintropin, disclosed in U.S. Pat. No. 5,614,492), LY-315902 (Lilly), GLP-1 (7-36)-NH2), AL-401 (AutoImmune), certain compositions as disclosed in U.S. Pat. No. 4,579,730, U.S. Pat. No. 4,849,405, U.S. Pat. No. 4,963,526, U.S. Pat. No. 5,642,868, U.S. Pat. No. 5,763,396, U.S. Pat. No. 5,824,638, U.S. Pat. No. 5,843,866, U.S. Pat. No. 6,153,632, U.S. Pat. No. 6,191,105, and WO 85/05029, and primate, rodent, or rabbit insulin including biologically active variants thereof including allelic variants, human insulin available in recombinant form (sources of human insulin include pharmaceutically acceptable and sterile formulations such as those available from Eli Lilly (Indianapolis, Ind. 46285) as Humulin™ (human insulin rDNA origin), also see the Physician's Desk Reference, 55.sup.th Ed. (2001) Medical Economics, Thomson Healthcare (disclosing other suitable human insulins).

In some cases an anti diabetic agent may comprise non-thiazolidinediones such as JT-501 and farglitazar (GW-2570/GI-262579), and pharmaceutically acceptable salts and esters thereof; PPARα/γ dual agonists such as AR-HO39242 (Aztrazeneca), GW-409544 (Glaxo-Wellcome), BVT-142, CLX-0940, GW-1536, GW-1929, GW-2433, KRP-297 (Kyorin Merck; 5-[(2,4-Dioxo thiazolidinyl) methyl]methoxy-N-[[4-(trifluoromethyl)phenyl]methyl] benzamide), L-796449, LR-90, MK-0767 (Merck/Kyorin/Banyu), SB 219994, muraglitazar (BMS), tesaglitzar (Astrazeneca), reglitazar (JTT-501) and the like.

In some cases an anti diabetic agent may comprise GSK 3β/GSK 3 inhibitors such as 4-[2-(2-bromophenyl)-4-(4-fluorophenyl-1H-imidazol-5-yl]pyridine and the like.

In some cases an anti diabetic agent may comprise dipeptidyl peptidase IV (DPP-IV) inhibitors, or peptides including amlintide and Symlin® (pramlintide acetate).

F. Evaluation Criteria of Biliary Function in NASH Subjects

As described herein, the methods and compositions of the present disclosure are useful for the treatment of subjects having fatty liver related disorders and are known, or suspected to have normal or substantially normal biliary tract function, by administration of an effective amount of ethyl eicosapentaenoic acid (EPA-E). The presence or absence of normal or substantially normal biliary tract function may be determined in a subject using any suitable methods known in the art. Generally, preferred tests for biliary tract function in NASH patients may be characterized in two groups: physiological based tests and biochemical based tests. Physiological based tests may include but are not limited to abdominal ultrasound, abdominal CT scan, endoscopic retrograde cholangiopancreatography (ECRP), Percutaneous transhepatic cholangiogram (PTCA) or Magnetic resonance cholangiopancreatography (MRCP). Biochemical based tests may include but are not limited to GGT tests, liver function tests, bilirubin tests, alkaline phosphatase (ALP) tests, liver enzyme tests, amylase blood test, lipase blood test, prothrombin time, and measurement of urine bilirubin. In some cases, one or more tests may be used to characterize biliary function. In some cases a combination of tests may be used to assess biliary function in NASH subjects.

i. Physiological Tests

Generally, the physiological tests, examples of which are provided herein, provide a visualization of the biliary duct, which may aid in the diagnosis of an obstruction. For example, if gallstones are present, these may be result in obstruction or partial obstruction of the biliary duct and the presence of gallstones may be visualized. In some cases visualization is achieved with X-rays (PTCA or abdominal CT), magnetic resonance (MRCRP) or ultrasound. In some cases, a direct obstruction may not be visualized. In some cases, these methods may indicate the narrowing of the biliary duct, or secondary effect of an obstruction. These may also aid in evaluating biliary function in a NASH subject.

ii. GGT Test

The GGT test is a common liver function enzyme test that measures the activity of the enzyme GGT. Blood test results for GGT suggest that the normal value is 8-78 IU/L (Merck Manual Appendix II), for men is 2-30 IU/L (Laboratory Reference Range Values) or 15-85 IU/L (*General Laboratory Manual*. Department of Pathology, Hackensack University Medical Centre. 2010. p. 117), whereas for women it is 1-24 IU/L (Laboratory Reference Range Values) or 5-55 IU/L (*General Laboratory Manual*. Department of Pathology, Hackensack University Medical Centre. 2010. p. 117).

In some cases, elevated serum GGT activity may be indicative of diseases of the liver, biliary system, and pancreas. In this respect, it is similar to alkaline phosphatase (ALP) tests, as described herein in detecting disease of the biliary tract. Both ALP and GGT may be used to as biochemical indicator of potential liver disease, although GGT tests generally provide increased sensitivity. Slightly elevated serum GGT may also been found to correlate with cardiovascular diseases in NASH subjects. GGT may accumulate in atherosclerotic plaques, and may circulate in blood in the form of distinct protein aggregates, some of which may indicate specific pathologies such as metabolic syndrome, alcohol addiction and chronic liver disease. High body mass index (BMI) may be associated with type 2 diabetes subjects with high serum GGT. Tests for GGT levels may be used alone or in combination with other tests to assess biliary tract function in NASH subjects.

iii. ALP Test

The ALP test is a common liver function enzyme test that measures the activity of the enzyme ALP. The normal range is 36-92 IU/L (Merck Manual Appendix II) or 20 to 140

IU/L (*General Laboratory Manual*. Department of Pathology, Hackensack University Medical Centre. 2010. p. 117) High ALP levels can show that the bile ducts are obstructed. Levels are significantly higher in children and pregnant women.

iv. Additional Biochemical Based Tests

Generally, any suitable biochemical tests may be used in the assessment of biliary function of NASH subjects. In some cases, tests, as part of a standard liver function panel, may be used to assess biliary function. In some cases, bilirubin tests may be useful to assess biliary function. One or more tests may be used in combination tests as provided herein in the assessment of biliary function.

iv. General Thresholds for Evaluating Biliary Function

The tests recommended for screening are the same as those for making the diagnosis, with the result that a positive screen is equivalent to a diagnosis of normal or substantially normal biliary function. In this case, normal or substantially normal may also comprise a subject being at risk for biliary disease. In some cases, biliary disease is diagnosed by having one or both of the following: 1) GGT equal to or more than 24, 25, 26, 27, 28, 29, 30, 31, 32, 33, 34, 35, 40, 45, 50, 55, 60 or 78 IU/L or GGT level equal to or less than 30 or 85 IU/L for men and GGT level equal to or less than 24 or 55 IU/L for women 2) an ALP test equal to or more than 92 or 140 IU/L. To get a diagnosis of abnormal biliary function, patients must satisfy one of the following criteria: 1) symptoms of biliary disease (i.e. narrowing or obstruction of the bial duct, weight loss, pain in the abdomen,) AND abnormal levels of GGT or ALP. Additional diagnostic criteria of one or more of these indicators may also indicate abnormal biliary function. In some cases, biliary disease is diagnosed by having serum direct bilirubin equal to or more than 0.3 or 0.4. Subjects having early stages of biliary disease may have levels at or about threshold levels as described herein.

III. PHARMACEUTICAL COMPOSITION

A. EPA-E Compositions

Eicosapentaenoic acid (EPA) is a known omega-3 polyunsaturated, long-chain fatty acid. Omega-3 fatty acids are known as components of oils, such as fish oil. A variety of commercial products are promoted as containing omega-3 fatty acids, or their esters, derivatives, conjugates and the like. Eicosapentaenoic acid (EPA) is also known as its ethyl ester form, ethyl eicosapentanoate (EPA-E). According to the present disclosure, EPA-E can be administered in a composition. EPA-E content in the total fatty acid of the compositions of the present disclosure are not particularly limited as long as the composition contains EPA-E as its effective component and intended effects of the present disclosure are attained, high purity EPA-E is preferably used.

The present disclosure may be a self-emulsifying composition comprising 50 to 95% by weight in total of EPA-E of preferably 60% by weight or more, more preferably 90% by weight or more, and still more preferably 96.5% by weight or more in total of the fatty acids and their derivatives. In some cases, the pharmaceutical composition may comprise at least about 40%, 46%, 50%, 60%, 70%, 80%, 90%, 95%, 96%, and 96.5% by weight of EPA-E in total of the fatty acids and their derivatives. In some cases, the pharmaceutical composition may comprise at most about 40%, 46%, 50%, 60%, 70%, 80%, 90%, 95%, 96%, and 96.5% weight of EPA-E in total of the fatty acids and derivatives. EPA-E can be administered to patients in a highly purified form, including the product known as Epadel® (Mochida Pharmaceutical Co., Ltd., Tokyo Japan) and pharmaceutically acceptable salts and esters thereof.

The EPA-E used in the present disclosure may be a synthetic, semi-synthetic, natural EPA-E, or a natural oil containing such EPA-E. Examples of the natural EPA-E include an extract from a natural oil containing an EPA-E, a crudely purified natural oil containing an EPA-E, and a highly purified natural oil containing an EPA-E produced by a method known in the art. Exemplary semi-synthetic EPA-E include EPA-E produced by a microorganism or the like and the EPA-E or the natural EPA-E which have been subjected to a chemical treatment such as esterification or ester exchange.

B. Formulation

In some embodiments, omega-3 fatty acids are formulated as a self-emulsifying composition. Self-emulsifying composition of the present disclosure may preferably have at least one of the effects including excellent self-emulsifying property, excellent dispersibility in the composition, excellent emulsion stability, excellent storage stability, excellent absorption property, and in particular, excellent absorption property and rate under fasting, and excellent convenience or compliance for the patients so that the composition can exhibit pharmacological effect of the EPA-E. In some cases, EPA-E may be combined with 5 to 50% by weight of an emulsifier having an HLB of at least 10.

In some cases, the pharmaceutical composition may comprise at least about 5%, 10%, 20%, 30%, 40%, and 50% emulsifier. In some cases, the pharmaceutical composition may comprise at most about 5%, 10%, 20%, 30%, 40%, and 50% emulsifier. The self-emulsifying composition is free from ethanol or the ethanol content is low. The present disclosure also provides a drug of such self-emulsifying composition, its production method, and the method of its use.

Examples of the pharmaceutically acceptable salts of the EPA-E include inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as mono-, di- and TG. Preferable examples include ethyl ester and TG ester, and the more preferred is ethyl ester. More specifically, preferable examples include EPA-E, TG ester of EPA-E, and the like.

The EPA-E used for the starting material of the self-emulsifying composition of the present disclosure is not particularly limited for its purity. The purity is typically such that content of the EPA-E in total of the fatty acids and their derivatives in the composition of the present disclosure could be preferably at least 40%, 50% or 60% by weight, more preferably at least 70% by weight, still more preferably at least 80% by weight, still more preferably at least 90% by weight, and most preferably at least 96.5% by weight. The EPA-E containing EPA-E and DHA-E at a high purity, for example, the one with the content of (EPA-E+DHA-E) in relation to the EPA-E of at least 50% by weight in total of the fatty acids and their derivatives is preferable, and the content is more preferably at least 60% by weight in total of the fatty acids and their derivatives, still more preferably at least 90% by weight in total of the fatty acids and their derivatives, and most preferably at least 98% by weight in total of the fatty acids and their derivatives. In other words, the composition of the present disclosure preferably has a high purity of EPA-E in the total fatty acid.

For example, when EPA-E and DHA-E are used, compositional ratio of EPA-E/DHA-E and content of (EPA-E+DHA-E) in relation to total fatty acid are not particularly limited as long as the purity of EPA in the composition of the present disclosure is in the range as described above. However, the compositional ratio of the EPA-E/DHA-E is preferably at least 0.8, more preferably at least 1.0, and most preferably at least 1.2.

The composition of the present disclosure may also contain a polyunsaturated fatty acid other than the EPA-E such as linoleic acid, γ linolenic acid, or dihomo-γ-linolenic acid or the pharmaceutically acceptable salt or ester thereof. However, content of arachidonic acid in the total of the fatty acids and their derivatives is preferably low, more preferably less than 2% by weight, still more preferably less than 1% by weight, and most preferably, the composition is substantially free from the arachidonic acid.

Compared to the fish oil or the fish oil concentrate, the EPA-E used in the composition or therapeutic agent of the present disclosure contains impurities such as saturated fatty acids and arachidonic acid which are unfavorable for cardiovascular events at a lower content, and this enables realization of the intended action without causing the problems of excessive nutrition or vitamin A intake. When the EPA-E in the form of ester is used, a sufficiently stable composition can be obtained by adding a commonly used antioxidant since the ester form has higher oxidation stability than the fish oils which are mainly TG form.

Purified fish oils may also be used for the EPA-E, and use of monoglyceride, diglyceride, and TG derivatives and combinations thereof of the EPA-E are also preferable embodiments. Various products containing the EPA-E are commercially available, for example, Incromega F2250, F2628, E2251, F2573, TG2162, TG2779, TG2928, TG3525, and E5015 (Croda International PLC, Yorkshire, England), and EPAX6000FA, EPAX5000TG, EPAX4510TG, EPAX2050TG, EPAX7010EE, K85TG, K85EE, and K80EE (Pronova Biopharma, Lysaker, Norway). These products may be purchased and used for the composition of the present disclosure.

In the present disclosure, the "polyoxyethylene hydrogenated castor oil" is a compound prepared by addition polymerization of ethylene oxide to the hydrogenated castor oil which is castor oil having hydrogen added thereto, Various compounds with different average degree of polymerization of ethylene oxide are commercially available, and examples include polyoxyethylene (20) hydrogenated castor oil (NTKKOL HCO-20, Nikko Chemicals Co., Ltd.), polyoxyethylene (40) hydrogenated castor oil (NIKKOL HCO-40, Nikko Chemicals Co., Ltd.), polyoxyethylene (50) hydrogenated castor oil (NIKKOL HCO-50, Nikko Chemicals Co., Ltd.), polyoxyethylene (60) hydrogenated castor oil (NIKKOL HCO-60, Nikko Chemicals Co., Ltd.), and polyoxyethylene (100) hydrogenated castor oil (NIKKOL HCO-100, Nikko Chemicals Co., Ltd.), and the preferred is polyoxyethylene (60) hydrogenated castor oil. These may be used alone or in combination of two or more. In the present disclosure, the "polyoxyethylene hydrogenated castor oil" includes all of such compounds unless otherwise noted.

In the present disclosure, the "polyoxyethylene sorbitan fatty acid ester" is polyoxyethylene ether of a fatty acid ester wherein a part of the hydroxy groups of anhydrous sorbitol have been esterified with a fatty acid. Various compounds with different esterified fatty acid are commercially available, and examples include polyoxyethylene (20) sorbitan monolaurate (NIKKOL TL-10, Nikko Chemicals Co., Ltd.), polyoxyethylene (20) sorbitan monopalmitate (NIKKOL TP-10V, Nikko Chemicals Co., Ltd.), polyoxyethylene (20) sorbitan monostearate (NIKKOL TS-10V, Nikko Chemicals Co., Ltd.), polyoxyethylene (20) sorbitan tristearate (NIKKOL TS-30V, Nikko Chemicals Co., Ltd.), polyoxyethylene (20) sorbitan monoisostearate (NIKKOL TI-10V, Nikko Chemicals Co., Ltd.), polyoxyethylene (20) sorbitan monooleate (NIKKOL TO-10V, Nikko Chemicals Co., Ltd.), and polyoxyethylene (20) sorbitan trioleate (NIKKOL TO-30V, Nikko Chemicals Co., Ltd.), and the preferred are polyoxyethylene (20) sorbitan monolaurate, polyoxyethylene (20) sorbitan monopalmitate, polyoxyethylene (20) sorbitan monostearate, and polyoxyethylene (20) sorbitan monooleate, and the more preferred are polyoxyethylene (20) sorbitan monooleate. These may be used alone or in combination of two or more, In the present disclosure, the "polyoxyethylene sorbitan fatty acid ester" includes all of such compounds unless otherwise noted.

In the present disclosure, the "polyoxyethylene castor oil" is a compound prepared by addition polymerization of ethylene oxide to castor oil. Various compounds having different average ethylene oxide mole number are commercially available, and examples include NIKKOL CO-3 with an average ethylene oxide mole number of 3 (Nikko Chemicals Co., Ltd.), NIKKOL CO-10 with an average ethylene oxide mole number of 10 (Nikko Chemicals Co., Ltd.), EMALEX C-20 with an average ethylene oxide mole number of 20 (Nippon Emulsion Co., Ltd.), EMALEX C-30 with an average ethylene oxide mole number of 30 (Nippon Emulsion Co., Ltd.), EMALEX C-40 with an average ethylene oxide mole number of 40 (Nippon Emulsion Co., Ltd.), and EMALEX C-50 with an average ethylene oxide mole number of 50 (Nippon Emulsion Co., Ltd.). These may be used alone or in combination of two or more. In the present disclosure, the "polyoxyethylene castor oil" includes all of such compounds unless otherwise noted.

In the present disclosure, the "polyethylene glycol fatty acid ester" is a fatty acid ester of a polyethylene glycol which is a fatty acid polymerized with ethylene oxide. Various compounds with different esterified fatty acid are commercially available, and examples include polyethylene glycol monolaurate (NIKKOL MYL-10, Nikko Chemicals Co., Ltd.), polyethylene glycol monostearate (NIKKOL MYS-10V, MYS-25V, MYS-40V, NYS-45V, and MYS-55V, Nikko Chemicals Co., Ltd.), polyethylene glycol monooleate (NIKKOL MYO-6 and MYO-10, Nikko Chemicals Co., Ltd.), polyethylene glycol distearate (NIKKOL CDS-6000P, Nikko Chemicals Co., Ltd.), and polyethylene glycol diisostearate (NIKKOL CDIS-400, Nikko Chemicals Co., Ltd.). These may be used alone or in combination of two or more. In the present disclosure, the "polyethylene glycol fatty acid ester" includes all of such compounds unless otherwise noted.

In the present disclosure, the "polyoxyethylene polyoxypropylene glycol" is a compound prepared by addition polymerization of ethylene oxide to the polypropylene glycol which is a polymerized propylene oxide. Various compounds having different average degree of polymerization of the propylene oxide and the ethylene oxide are commercially available, and examples include polyoxyethylene (3) polyoxypropylene (17) glycol (Adeka Pluronic L-31, ADEKA), polyoxyethylene (20) polyoxypropylene (20) glycol (Adeka Pluronic L-44, ADEKA), polyoxyethylene (42) polyoxypropylene (67) glycol (Adeka Pluronic P-123, ADEKA), polyoxyethylene (54) polyoxypropylene (39) glycol (Newdet PE-85, Sanyo Chemical Industries, Ltd.), polyoxyethylene (105) polyoxypropylene (5) glycol (PEP101, Sanyo Chemical Industries, Ltd.), polyoxyethylene (120)

polyoxypropylene (40) glycol (Adeka Pluronic F-87, ADEKA), polyoxyethylene (160) polyoxypropylene (30) glycol (Adeka Pluronic F-68, ADEKA), polyoxyethylene (196) polyoxypropylene (67) glycol (Lutrol F127, BASF Japan), and polyoxyethylene (200) polyoxypropylene (70) glycol, and the preferred is polyoxyethylene (105) polyoxypropylene (5) glycol. These may be used alone or in combination of two or more. In the present disclosure, the "polyoxyethylene polyoxypropylene glycol" includes all of such compounds unless otherwise noted.

In the present disclosure, the "sucrose fatty acid ester" is an ester of sugar and a fatty acid. Various compounds with different types of the esterified fatty acids and degree of esterification are commercially available, and examples include Surfhope SE PHARMA J-1216 containing 95% of lauric acid in the fatty acid (Mitsubishi-Kagaku Foods Corporation), Surfhope SE PHARMA J-1416 containing 95% of myristic acid in the fatty acid (Mitsubishi-Kagaku Foods Corporation), Surfhope SE PHARMA J-1615 and J-1616 containing 80% of palmitic acid in the fatty acid, (Mitsubishi-Kagaku Foods Corporation), J-1811, J-1815, and J-1816 containing 70% of stearic acid in the fatty acid (Mitsubishi-Kagaku roods Corporation), and Surfhope SE PHARMA J-1715 containing 70% of oleic acid in the fatty acid, which may be used alone or in combination of two or more. The "sucrose fatty acid ester" used in the present disclosure include all of such compounds.

The emulsifier added to a self-emulsifying composition of the present disclosure may have an HLB of at least 10, preferably at least 11, and more preferably at least 12.

Total content of the emulsifier having an HLB of at least 10 in a self-emulsifying composition of the present disclosure is not particularly limited as long as it is at least 10 parts by weight in relation to 100 parts by weight of the EPA-E. The content is typically 10 to 100 parts by weight, preferably 10 to 80 parts by weight, and more preferably 10 to 50 parts by weight in relation to 100 parts by weight of the EPA-E.

In the present disclosure, the "lecithin" is a type of glycerophospholipid, and examples include soybean lecithin, enzymatically decomposed soybean lecithin, hydrogenated soybean lecithin, egg yolk lecithin, hydrogenated phospholipid, phospholipid from milk, lysolecithin, phosphatidyl choline, and phosphatidyl serine. The preferred are soybean lecithin, enzymatically decomposed soybean lecithin, hydrogenated soybean lecithin, and egg yolk lecithin, and the more preferred are soybean lecithin. These may be used alone or in combination of two or more. In the present disclosure, the "lecithin" includes all of such compounds unless otherwise noted.

Commercially available products include purified soybean lecithin (Nisshin Oilio), purified egg yolk lecithin (Asahi Kasei Pharma Corporation), and egg yolk lecithin PL-100M (Kewpie Corporation), and use of such product is also possible.

In the present disclosure, the "polyhydric alcohol" is a polyol compound having the structure of a straight chain or cyclic aliphatic hydrocarbon wherein two or more carbon atoms are each substituted with one hydroxy group. Exemplary such polyhydric alcohols include divalent alcohols such as ethyleneglycol, propylene glycol, trimethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexane triol, and polyhydric alcohol polymers such as diethylene glycol, dipropylene glycol, triethylene glycol, polyethylene glycol, polypropylene glycol, and polyglycerin, and the preferred are propylene glycol or glycerin. In the present disclosure, the "polyhydric alcohol" includes all of such compounds unless otherwise noted.

Total amount of the lecithin and/or the polyhydric alcohol added in the self-emulsifying composition of the present disclosure is not particularly limited. However, the total amount of the lecithin and/or the polyhydric alcohol is typically 0 to 50 parts by weight, preferably 3 to 40 parts by weight, and more preferably 5 to 30 parts by weight in relation to 100 parts by weight of the EPA-E.

The ethanol in the self-emulsifying composition of the present disclosure is preferably used at an amount not causing quality change in the course of capsulation, distribution, or storage, at an amount not causing change in the content of the capsule, and at an amount not exceeding the established upper limit of the daily dose as a drug. The ethanol content is typically up to 10% by weight, preferably up to 4% by weight, more preferably up to 1% by weight, more preferably up to 0.5% by weight, more preferably up to 0.2% by weight, still more preferably up to 0.1% by weight, and most preferably 0% by weight (no ethanol addition).

Preferable ethanol concentration can be adequately determined in consideration of the EPA-E concentration in the self-emulsifying composition and the daily dose. When the self-emulsifying composition of the present disclosure is orally administered at a daily dose in terms of the EPA-E of 1800 mg, and for example, the preparation contains 75% by weight of the EPA-E, the maximum daily dose of 3.26 mg described in "Dictionary of Drug Additives (in Japanese)" will not be exceeded when the ethanol content is not more than 0.135% by weight.

The preferable embodiment of the self-emulsifying composition of the present disclosure containing such EPA-E and an emulsifier is a combination of EPA-E and/or DHA-E with at least one emulsifier selected from the group consisting of polyoxyethylene hydrogenated castor oil, polyoxyethylene sorbitan fatty acid ester, polyoxyethylene castor oil, sucrose fatty acid ester, and lecithin. When the self-emulsifying composition of the present disclosure is used as a food such as special purpose food, functional health food, and health food, the preferred is the combination of EPA-E and/or DHA-E with a sucrose fatty acid ester and/or a lecithin which has good results as a food additive. When a sucrose fatty acid ester is used, the preferable amount is 1% by weight to 20% by weight, more preferably 4% by weight to 20% by weight, and most preferably 4% by weight to 10% by weight in the self-emulsifying composition. The most preferable embodiments are a combination of EPA-E and polyoxyethylene (50) hydrogenated castor oil or polyoxyethylene (60) hydrogenated castor oil; a combination of EPA-E and polyoxyethylene (20) sorbitan monooleate; a combination of EPA-E and polyoxyethylene castor oil; and a combination of EPA-E and sucrose fatty acid ester J-1216 or J-1816.

Also preferred is the further combination with a lecithin such as soybean lecithin and/or a polyhydric alcohol such as propylene glycol.

When the emulsifier is at least one member selected from the group consisting of polyoxyethylene hydrogenated castor oil, polyoxyethylene sorbitan fatty acid ester, and polyoxyethylene castor oil, the polyhydric alcohol is preferably a dihydric alcohol, and use of propylene glycol is more preferable. When the emulsifier is a sucrose fatty acid ester, the polyhydric alcohol is preferably a trihydric alcohol, and use of glycerin is more preferable.

Preferably, the composition and therapeutic agent of the present disclosure is substantially free from water. The "substantially free from water" means that the water content is up to 10% by weight, preferably up to 5% by weight, and even more preferably up to 3% by weight.

The self-emulsifying composition of the present disclosure may also contain additives such as an emulsion aid, stabilizer, antiseptic, surfactant, and antioxidant. Exemplary emulsion aids include fatty acids containing 12 to 22 carbon atoms such as stearic acid, oleic acid, linoleic acid, palmitic acid, linolenic acid, and myristic acid and their salts. Exemplary stabilizers include phosphatidic acid, ascorbic acid, glycerin, and cetanols, and exemplary antiseptics include ethyl paraoxybenzoate and propyl paraoxybenzoate. Exemplary surfactants include sucrose fatty acid esters, sorbitan fatty acid esters, glycerin fatty acid esters, polyglycerin fatty acid esters, polyoxyethylene sorbitan fatty acid esters, polyoxyethylene alkyl ethers, polyoxyethylene fatty acid esters, polyoxyethylene alkyl phenyl ethers, and polyoxyethylene polyoxypropylene alkyl ethers having an HLB of less than 10. Exemplary antioxidants include oil-soluble antioxidants such as butylated hydroxy toluene, butylated hydroxy anisole, propyl gallate, propyl gallate, pharmaceutically acceptable quinone, astaxanthin, and α-tocopherol.

In addition, an adequate carrier or mediator, a colorant, a flavor, and optionally, a vegetable oil or an additive such as non-toxic organic solvent or non-toxic solubilizing agent (for example glycerin), emulsifier, suspending agent (for example, Tween 80 and gum arabic solution), isotonic agent, pH adjusting agent, stabilizer, corrective, flavoring agent, preservative, antioxidant, or absorption promoter commonly used in the art may be adequately combined to prepare an appropriate pharmaceutical preparation.

More specifically, since the EPA-E is highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition. Storage temperature is preferably room temperature, and frozen storage is preferably avoided since the freezing may result in the loss of self-emulsifying property, dispersibility in the composition, or emulsion stability.

The self-emulsifying composition of the present disclosure can be produced by mixing the EPA-E, the emulsifier having an HLB of at least 10, and the optionally added components such as lecithin, polyhydric alcohol, and antioxidant with optional heating to dissolve the components.

In some cases, the pharmaceutical composition may comprise additional elements which may include but are not limited to antihypertensives such as angiotensin II receptor blockers such as irbesartan, olmesartan medoxomil, candesartan cilexetil, telmisartan, valsartan, and losartan potassium; angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine; a receptor blocker such as tolazoline, and phentolamine; β receptor blockers such as atenolol, metoprolol, acebutolol, propranolol, pindolol, carvedilol, and labetalol hydrochloride; a receptors stimulant such as clonidine and methyldopa; and diuretics such as eplerenone, hydrochlorothiazide, and furosemide.

In some cases, the pharmaceutical composition may comprise additional elements which may include but are not limited to antidiabetics as described herein.

In some cases, the pharmaceutical composition may comprise additional elements which may include but are not limited to vitamins such as ascorbic acid (vitamin C), tocopherol (vitamin E), and tocopherol nicotinate, and N-acetylcysteine, probucol.

In some cases, the pharmaceutical composition may comprise additional elements which may include but are not limited to blood flow improving agents such as cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, hepronicate, and shimotsu-to extract.

In some cases, the pharmaceutical composition may comprise additional elements which may include but are not limited to bile acid derivatives such as ursodeoxycholic acid, chenodeoxycholic acid, bile powder, deoxycholic acid, cholic acid, bile extract, bear bile, oriental bezoar, and dehydrocholic acid. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin.

C. Administration and Dosage

Compositions comprising EPA-E useful for the disclosure include commercially available compositions of EPA-E, such as Epadel®, Lovaza™, Omacor™, Lotriga™ or Vascepa™ noted above. Compositions comprising EPA-E may be administered in tablet, capsule, powder or any other solid oral dosage form, as a liquid, as a soft gel capsule or other capsule form, or other appropriate and convenient dosage forms for administration to a patient in need thereof. Compositions can also include pharmaceutically acceptable excipients known to those of ordinary skill in the art including surfactants, oils, co-solvents or combinations of such excipients, together with stabilizers, emulsifiers, preservatives, solubilizers and/or other non-active pharmaceutical ingredients known to those of skill in the art relative to the preparation of pharmaceutical compositions.

The dose and dosage period of the EPA-E used in the composition of the present disclosure is a dose and period sufficient for realizing the intended action, which may be adequately adjusted depending on the administration route, frequency of administration per day, seriousness of the symptoms, body weight, age, and other factors.

A composition of the present disclosure may be administered to the patient orally, endorectally, or transvaginally. However, oral administration is preferable in the case of the patient who can take the drug orally, and the composition may be administered in the form of a jelly preparation in the case of patients undergoing dialysis or patients with aphagia by jelling the composition with gelatin or the like.

Doses of the aforementioned compositions as the active ingredient can be suitably decided depending on the purpose of administration, i.e., therapeutic or preventive treatment, nature of a disease to be treated or prevented, conditions, body weight, age, sexuality and the like of a patient. The practically desirable method and sequence for administration varies depending on the purpose of administration, i.e., therapeutic or preventive treatment, nature of a disease to be treated or prevented, conditions, body weight, age, sexuality and the like of a patient. The optimum method and sequence for administration of the compounds described in detail herein under preset given conditions may be suitably selected by those skilled in the art with the aid of the routine technique and the information contained in the present specification and field of invention.

In the case of oral administration, the composition may be administered at a dose in terms of the EPA-E of 0.1 to 5 g/day, preferably 0.2 to 3 g/day, more preferably 0.4 to 2.0 g/day, and most preferably 0.6 to 1.0 g/day in 1 to 3 divided doses. However, the entire dose may be administered at once or in several divided doses. While meal affects absorption of the EPA-E, and the administration of the EPA-E is preferably conducted during the meal or after the meal, and more preferably immediately after the meal (within 30 minutes after the meal), the self-emulsifying composition of the present disclosure has excellent absorption under fasting, and therefore, it exhibits the intended effects even when administered at a timing other than during, after, or immediately after the meal, for example, before or immediately before the meal or before going to the bed; to patients with reduced absorption ability of the intestinal tract (for example, elderly, patients of intestinal disease, patients after intestinal surgery, terminal cancer patients, or patients taking a lipase inhibitor); or used at a reduced dose.

The compositions of EPA-E are administered according to the disclosure to a subject or patient to provide the patient with a dosage of about 0.3-10 g per day of EPA-E, alternatively 0.5-8 g per day, alternatively 0.6-6 g per day, alternatively 1-4-g per day, alternatively 0.9-3.6 g per day or specifically about 1800 mg per day or about 2700 mg per day of EPA-E.

The composition to be administered can contain other fatty acids, especially any omega-3 unsaturated fatty acid, especially DHA-E. The ratio of EPA-E/DHA-E in the composition, the content of EPA-E and DHA-E in the total fatty acids and administration amount of EPA-E and DHA-E are not limited but the ratio is preferably 0.8 or more, more preferably 1.0 or more, still more preferably 1.2 or more. The composition is preferably highly purified; for example, the proportion of EPA-E+DHA-E in the fatty acids and their derivatives is preferably 40% by weight or more, more preferably 80% by weight or more, and still more preferably 90% by weight or more. The daily amount in terms of EPA-E+DHA-E is typically 0.3 to 10.0 g/day, preferably 0.5 to 6.0 g/day, and still more preferably 1.0 to 4.0 g/day. The low content of other long chain saturated fatty acids is preferred, and among the long chain unsaturated fatty acids, the content of omega-6 fatty acids, and in particular, the content of arachidonic acid in total of the fatty acids and their derivatives is preferably as low as less than 2% by weight, and more preferably less than 1% by weight. For example, soft capsule (Lovaza™, Omacor™ and Lotriga™) containing about 46% by weight of EPA-E and about 38% by weight of DHA-E is commercially available in the U.S. and other countries as a therapeutic agent for hypertriglyceridemia and soft capsule (Vascepa™) containing at least 96% by weight of EPA-E is commercially available in the U.S as a therapeutic agent for hypertriglyceridemia.

Patients treated for NASH can be administered EPA-E according to the disclosure for 3, 6 or 9 months, or for 1 year, 2 years or more and can be administered EPA-E in one, two or three dosage per day, or other multiple doses per day including 1 to about 10, 1 to 8, 1 to 6, 1 to 4 or 1 to 2 dosage units per day as appropriate for patient therapy. The term "dose unit" and "dosage unit" herein refer to a portion of a pharmaceutical composition that contains an amount of EPA-E for a single administration to a subject.

When orally administered at such dose, the administration period may be adequately determined depending on the target disease and degree of symptoms. For example, in the case of administration for NASH, the administration period is not particularly limited as long as improvements of biochemical markers related to NASH, improvement in the pathological conditions or therapeutic effects, and suppression of the progress in metabolic syndrome, cardio or cerebrovascular event, or ulcer and gangrene of extremities and peripheries are realized. However, administration period is determined to realize the improvements in the concentration of plasma lipid marker (total cholesterol (hereinafter abbreviated as Cho), TG, postprandial TG, low-density lipoprotein Cho, high-density lipoprotein Cho, very-low-density lipoprotein Cho, non-high-density lipoprotein Cho, intermediate-density lipoprotein Cho, very-high-density lipoprotein Cho, free fatty acid, phospholipid, chylomicron, ApoB, lipoprotein (a), remnant-like lipoprotein Cho, small dense low-density lipoprotein Cho, etc.), increase in the skin temperature of extremities and peripheries which can be measured by thermography or the like, increase in the walking distance, increase in the serum CPK or other test value, and improvement of various symptoms such as numbness, coldness, ache, pain at rest, itching, cyanosis, flare, chilblain, neck stiffness, anemia, poor complexion, itching, and crawling. The amelioration or therapeutic effects may be monitored by other biochemical, pathological, or symptomatic parameters related to NASH. The administration is preferably continued as long as abnormality is observed in biochemical index such as serum lipid concentration or pathology. In addition, the composition may be administered every alternate day or 2 or 3 days in a week, or as the case may be, a drug withdrawal period of about 1 day to 3 month, and more preferably about 1 week to 1 month may be included.

If indicated by the physician, oral administration may be started at a dose lower than the recommended daily EPA-E dose at the first day, and then, the dose may be gradually increased to the maximum daily dose as the maintenance dose. The dose may be reduced depending on the conditions of the patient. Lower daily dose is preferable in view of reducing the side effects, and administration of once or twice a day is preferable in view of the drug compliance.

The method of the present invention may administer a therapeutically effective amount of a pharmaceutical composition comprising EPA-E in combination with a second effective component. The second effective component may be adequately determined depending on the target disease and the seriousness of the symptom. However, the second effective component is preferably a component that does not adversely affect the effects of EPA-E, and examples include therapeutic agent for hyperlipidemia, antihypertensives, antidiabetics, antioxidants, blood flow improving agents, and bile acid derivatives.

Of the preferable examples of the second effective component, exemplary therapeutic agents for hyperlipidemia include polyenephosphatidylcholine, unsaponifiable soybean oil (soy sterol), gamma-oryzanol, riboflavin butyrate, dextran sulfate sodium sulfur 18, pantethine, and elastase; statins such as pravastatin, simvastatin, atorvastatin, fluvastatin, pitavastatin, rosuvastatin, and cerivastatin; fibrates such as simfibrate, clofibrate, clinofibrate, bezafibrate, and fenofibrate; lipolytic enzyme inhibitors such as orlistat and cetilistat; resins such as colestyramine and colestimide; and ezetimibe.

Exemplary antihypertensives include angiotensin II receptor blockers such as irbesartan, olmesartan medoxomil, candesartan cilexetil, telmisartan, valsartan, and losartan potassium; angiotensin-converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipine; [alpha] receptor blocker such as tolazoline, and phentolamine; [beta] receptor blockers such as atenolol, metoprolol, acebutolol, propranolol, pindolol, carvedilol, and labetalol hydrochloride; a receptors stimulant such as clonidine and methyldopa; and diuretics such as eplerenone, hydrochlorothiazide, and furosemide.

Exemplary antidiabetics include [alpha]-glucosidase inhibitors such as acarbose, voglibose, and miglitol; sulfonyl urea hypoglycemics such as gliclazide, glibenclamide, glimepiride, and tolbutamide; fast-acting insulin secretagogues such as nateglinide and mitiglinide; biguanide hypoglycemics such as metformin hydrochloride and buformin hydrochloride; dipeptidyl phosphatase 4 inhibitors such as sitagliptin, vildagliptin, alogliptin, linagliptin and saxagliptin; thiazolidine reagents such as pioglitazone hydrochloride and rosiglitazone maleate; and glucagon-like peptide 1 derivative reagents such as exenatide, lixisenatide and liraglutide.

Exemplary antioxidants include vitamins such as ascorbic acid (vitamin C), tocopherol (vitamin E), and tocopherol nicotinate, and N-acetylcysteine, probucol.

Exemplary blood flow improving agents include cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesilate, tolazoline hydrochloride, heproniｃate, and shimotsu-to extract.

Exemplary bile acid derivatives include ursodeoxycholic acid, chenodeoxycholic acid, bile powder, deoxycholic acid, cholic acid, bile extract, bear bile, oriental bezoar, and dehydrocholic acid. Preferable examples also include biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched chain amino acids such as leucine, isoleucine, and valine, calcium, iron, zinc, copper, and magnesium. Other examples include components used in designated health foods and functional nutritional foods such as soy protein, chitosan, low molecular weight sodium alginate, dietary fiber from psyllium seed coat, soy peptide with bound phospholipids, phytosterol ester, plant stanol ester, diacylglycerol, globin digest, and tea catechin.

D. Treatment Effects

The compositions of the present disclosure can be used as a therapeutic agent for various diseases of animals, and in particular, mammals, for example, therapeutic agent for NASH and related disorders. The compositions of the present disclosure are particularly expected to exhibit amelioration or therapeutic effects in NASH subjects without diabetes, or with pre-diabetes or mild diabetes, or without biliary tract disease, or in the early stages of the disease. NASH subjects may improve or maintain a variety of symptoms, which may include but are not limited to, increase in blood lipid, expression of insulin resistance, increase in blood pressure, abnormal liver function tests, abnormal liver enzyme activity, elevated glucose levels, liver dysfunction, hyperlipidemia, or any abnormal criteria as found in FIG. 5. In some cases, the pharmaceutical composition may aid in maintaining a function, level or activity present in a subject.

In some cases, the compositions may lower fasting glucose levels by methods as provided by the disclosure. In some cases, the composition may lower glucose levels as determined to be above normal, as would be found in pre-diabetic and mildly diabetic subjects. In some cases, the composition may lower high glucose levels in subjects not considered to have diabetes. In some cases, the pharmaceutical composition may aid in maintaining a glucose level present in a subject.

In some cases, the composition may lower GGT levels lower than the thresholds as provided by the disclosure. In some cases, the composition may lower GGT levels as determined to be above normal, as would be found in NASH subjects having biliary disease or be at risk for the disease. In some cases, the composition may lower GGT levels in subjects not considered to have biliary disease. In some cases, the pharmaceutical composition may aid in maintaining a GGT level present in a subject.

The compositions of the present disclosure can reduce burden of the patients by reducing the dose and daily frequency of the administration, and hence, by improving the drug compliance. This also results in the higher effects of amelioration or treatment.

IV. EXAMPLES

Example 1: Pre-Clinical Experience

In animal and in vitro model studies, EPA-E (ethyl all-cis-5,8,11,14,17-eicosapentaenoate) has been shown to lower lipids in rats, hamsters and rabbits; have anti-aggregation effects on platelets from rats, rabbits and humans; and to preserve the elasticity of arteries in rabbits. In other studies, polyunsaturated fatty acids (PUFAs) have been shown to ameliorate hepatic steatosis in ob/ob mice through down-regulation of hepatic nuclear sterol regulatory element binding protein-1c (SREBP-1c). In a similar manner, EPA-E following repeat oral administration at ≥0.1 mg/g suppressed fat accumulation in a mouse diet-induced hepatic steatosis model by suppressing hepatic SREBP-1c levels as well as monounsaturated fatty acid (MUFA) synthesis by stearoyl-Coenzyme A desaturase 1 (SCD1). In a galactosamine-induced steatohepatitis mouse model, EPA-E after oral administration at 1000 mg/kg retarded progression of steatohepatitis by suppressing triglyceride (TG) accumulation. EPA-E following repeat oral administration at 1000 mg/kg inhibited fibrosis by suppressing inflammation and oxidative stress in a methionine-choline deficient diet rat model of nonalcoholic steatohepatitis.

In safety pharmacology studies, at oral doses up to 3000 mg/kg, EPA-E had no effect on the central nervous, autonomic nervous, respiratory and cardiovascular systems except for a reduction in gastric fluid levels in pylorus-ligated rats after a 3000 mg/kg oral dose. The effects of the metabolites and impurities of EPA-E as well as oxidized EPA-E on the above systems were not marked and do not appear to significantly contribute to general pharmacological effects of EPA-E.

Pharmacokinetics and Product Metabolism in Animals Summary

EPADEL is a product containing ethyl all-cis-5,8,11,14, 17-eicosapentaenoate (EPA-E), one of the n−3 essential fatty acids. The preclinical absorption, distribution, metabolism and excretion (ADME) characteristics of EPA-E have been determined primarily in rats.

Oral administration of a single dose of radioactive $^{14}$C-EPA-E at the dose of 30-1000 mg/kg in rats showed that EPA-E was well-absorbed, mainly through the lymphatic route. After administration of $^{14}$C-EPA-E into the ligated intestine of rats, the residual radioactivity in the intestine at 24 hours was only 4.6% of the administered dose. Radioactivity transferred to the plasma and lymph was mainly detected in the triglyceride (TG) fraction in the early phase after dosing, while distribution to the free fatty acid (FFA) fraction was slight at all timepoints. The radioactivity was widely distributed in the body tissues; relatively high levels were observed especially in the brown fat, adrenal, liver and pancreas. Within the tissues, the radioactivity was mainly distributed in the TG and/or phospholipid (PL) fractions. $^{14}$C-EPA-E was hydrolyzed rapidly in the small intestine homogenates, lymph, plasma and liver homogenates of the rat. Orally administered EPA-E was primarily incorporated in adrenal gland lipids as cholesterol esters of the fatty acids eicosapentaenoic acid (EPA), docosapentaenoic acid (DPA) and docosahexaenoic acid (DHA).

The uptake of $^{14}$C-EPA-E-derived radioactivity in rats described above is compatible with the absorption process of essential fatty acids in animals and humans described below. In addition, esterases are also distributed in most of the organs in humans). Therefore, the absorption and distribution profiles after oral dosing of EPA-E should be qualitatively similar in humans and dogs as observed in rats.

The digestion and absorption of essential fatty acids, mainly in the form of TG, are known to involve several processes.

The fatty acids are rapidly hydrolyzed from the TG to FFA by lipase in the intestine.

The FFA are taken up by the enterocytes where they are re-esterified into TG and enter the blood circulation, mainly through the lymphatic route as chylomicrons.

In the tissues, the TG of the chylomicrons is hydrolyzed again by lipoprotein lipase to FFA and taken up by the tissues.

Consequently, when EPA-E is administered orally to humans, it would appear that it is well absorbed, even though the unchanged ethyl ester form is not detected, and the free form (EPA) is only detected at a very low level, in the blood. Due to this absorption mechanism of essential fatty acids, the administered EPA-E exists as a blood-constituent fatty acid in the total lipids. In fact, according to the approval package document of Lovaza®, the free form of EPA is undetectable in the circulation (<1 µM) following an oral dose of 4 g of Omacor® (a mixture of the ethyl esters of EPA and DHA) Following oral administration of EPA-E, EPA, DPA and DHA were isolated and identified as metabolites in tissues and plasma. EPA, DPA and DHA were incorporated into TG and PL. Radioactivity was primarily excreted in expired air (44%) after single oral administration at 30 mg/kg EPA-E with minimal excretion in bile and urine (~3%) and approximately 20% excreted in feces. Thus, the respiratory route (as $^{14}$CO2) was considered to be the major elimination pathway of $^{14}$C-EPA-E. Excretion of radioactivity in dogs after single oral administration at 30 mg/kg was low with 1.0% excreted in the urine and 19.2% recovered in the feces after 1 week.

Renal excretion was the elimination route for several minor highly polar metabolites (<0.4%), but EPA-E, EPA, DPA or DHA were not detected in the urine. In feces, EPA-E and EPA, evidently derived from the unabsorbed drug, were detected; however, no DPA or DHA was detected in the feces.

In metabolism studies conducted in vitro, when $^{14}$C-EPA-CoA was incubated with the rat liver mitochondrial fraction, 17.1% of the radioactivity added to the incubation mixture was detected as $^{14}$CO2 and the formation of carbon chain-shortened products was observed. Incubation of $^{14}$CEPA-CoA with a rat peroxisome fraction also resulted in the formation of carbon chain-shortened products. These results show that EPA, after being taken up by the rat tissues, is finally almost entirely oxidized to CO2 by mitochondrial and peroxisomal β-oxidation.

After oral administration of $^{14}$C-EPA-E to the rat, EPA, DPA and DHA were detected as metabolites in the total lipid fraction of the plasma and tissues (liver, fat, heart and brain). However, no unchanged EPA-E was found in the plasma or any of the tissues. In the total lipid fraction of the liver, the radioactivity originated mainly from EPA, DPA and DHA. Thus, it is considered that EPA, DPA and DHA are the predominant metabolites of $^{14}$C-EPA-E in tissues, as constituent fatty acids of the total lipid fraction. When $^{14}$C-EPA-K was incubated with the microsomal fraction, formation of DPA and DHA was detected. These results show that EPA taken up by the rat tissues is elongated to DPA and DHA in the microsomes.

Plasma protein binding in rats and dogs was >86% and >96%, respectively. Previous studies have shown that EPA is unlikely to inhibit CYP450 at free concentrations observed in humans.

Example 2: Clinical Trial Data

Study Design

This example provides the protocol used for an ongoing phase II clinical trial, double blind, placebo-controlled study to investigate the safety, efficacy, and pharmacokinetic profile of two doses of EPA-E in subjects with NASH. Up to 70 subjects were enrolled into each treatment arm, for a total of 210 subjects to be enrolled. Block randomization using an interactive voice response system (IVRS) was used to assign patients in a 1:1:1 ratio to two active doses and placebo. Patients were stratified at randomization by presence or absence of diabetes. Patients with diabetes comprised no more than 25% of the total number of patients enrolled. Subjects were treated with 600 mg EPA-E, 900 mg EPA-E or placebo three times a day for one year.

Study arm 1: 600 mg EPA-E (3 capsules), TID
Study arm 2: 900 mg EPA-E (3 capsules), TID
Study arm 3: placebo (3 capsules), TID Subjects were required to have a liver biopsy with proven NASH in the 6 month period prior to screening. The Pharmacokinetic profile for EPA-E was evaluated in a subgroup of subjects in specified sites. Subjects were approached prior to providing informed consent to determine if they will participate in the PK group subset. Approximately 36 subjects participated in the PK subset evaluation (12 from each treatment arm, to include 6 males and 6 females).

A study schematic is provided in FIG. 6. Overall study duration plan was 2 years.

The Investigational Drugs

In order to support the trial, EPA-E capsules and matching placebo capsules were prepared. EPA-E capsule is an oval soft gelatin capsule containing 300 mg of EPA-E as an active ingredient. Placebo capsule is an oval soft gelatin capsule containing olive oil as an inactive ingredient. These capsules are unidentifiable as EPA-E capsules or placebo capsules.

Subjects were administered orally 3 capsules 3 times daily, immediately after meals.

Eligibility Criteria

Subjects with a histological diagnosis of NASH are eligible.

Inclusion Criteria

Inclusion criteria were designed to ensure that subjects with biopsy proven NASH are included, and to avoid situations where potential harm may occur to subjects in conjunction with participation in the study.

Subjects were potentially included into the study if they met all the following criteria:
1. Diagnosis of definite NASH by the central reading pathologists:
   Liver biopsy slides will be submitted for evaluation by the central pathologists according to one of the following criteria:
   a. Previous liver biopsies must have been obtained within 6 months prior to informed consent and should be judged by the local pathologist as showing NAS ≥4 with a minimum score of 1 each for steatosis and lobular inflammation plus EITHER ballooning OR at least 1a sinusoidal fibrosis AND a finding of possible or definite steatohepatitis
   b. For liver biopsies performed after informed consent is obtained, all slides will be submitted for reading by the central pathologists in conformity with the independent pathology review charter (IPRC)
2. Patients of either gender greater than 18 years of age
3. Patients with diabetes that have been on stable doses of anti-diabetic agents since at least 6 months prior to liver biopsy may be enrolled
4. Females must be of non-child bearing potential (surgically sterilized or at least two years post-menopausal) or if of child-bearing potential, must have a negative pregnancy test at screening and agree to use an effective form of contraception during the study and for at least 30 days following the last dose of study medication
5. Normal ECG or clinically non-significant findings at the Screening and Baseline visits
6. No significant concomitant medical illness, without any clinically significant physical exam findings and without any clinically significant laboratory findings, as determined by the principal investigator
7. Signed an informed consent form indicating that they understand the purpose of and procedures required for the study and are willing to participate in the study and comply with the study procedures and restrictions Exclusion Criteria Exclusion criteria have been designed to exclude subjects from the study if they will not be evaluable for the primary endpoint, if they have disease states that would interfere with analysis of study endpoints, or would put subjects at risk of serious adverse events associated with their participation.

Potential subjects will be excluded from participating in the study if they meet any of the following exclusion criteria:
1. Inability or unwillingness to have a liver biopsy
2. Diagnosis of cirrhosis by central pathology reviewers
3. Previous bariatric surgery or biliary diversion (i.e. gastric bypass), esophageal banding and gastric banding
4. Serum ALT>300 U/L
5. Subject has used drugs associated with steatohepatitis within 6 months prior to screening (corticosteroids, high dose estrogens, methotrexate, amiodarone, anti-HIV drugs, tamoxifen, diltiazem)
6. Use of the following anti-NASH agents for more than a 2 week period in the 3 months prior to liver biopsy or the 3 months prior to screening:
   a. Vitamin E>60 IU per day
   b. Omega-3-acid ethyl esters or omega-3-PUFA-containing supplements >200 mg per day
   c. Thiazoledinediones (e.g. pioglitazone)
7. Patients on a non-stable dose of the following anti-NASH agents within 6 months of the liver biopsy or within 6 months of the screening visit: HMG-CoA reductase inhibitors (statins), fibrates, probucol, ezetimibe, ursodiol (UDCA), taurine, betaine, Nacetylcysteine, s-adenosylmethionine (SAM-e), milk thistle, anti-TNF therapies, or probiotics
8. Greater than a 10% decrease in weight within 8 weeks of baseline visit
9. Alcohol consumption >30 g/day, currently or for more than 3 consecutive months within 5 years of screening
10. Blood alcohol level greater than 0.02% at screening and/or baseline
11. Evidence of active substance abuse, including prescription and recreational drugs
12. Other liver disease (hepatitis C, hepatitis B, Wilson's, autoimmune, α-1-antitrypsin and hemochromatosis) or known HIV infection
13. Pregnant or lactating at the screening visit
14. Renal insufficiency (creatinine >2 mg/dL), symptomatic coronary, peripheral or neurovascular disease, symptomatic heart failure (NYHA 2-4) or advanced respiratory disease requiring oxygen therapy
15. History of cerebral or retinal hemorrhage or other bleeding diathesis
16. QTc >450 msec for males and >470 for females as corrected by the Fridericia formula
17. Inability to provide written informed consent
18. Received any investigational agent or participation in any clinical study of an investigational agent or investigational therapy within 3 months prior to the screening visit.
19. Any condition in the opinion of the Principal Investigator that would contraindicate the patient's participation Prohibited and Concomitant Medications All prescription and over-the-counter medications taken by subjects during the 30 days before screening up to the start of treatment were recorded. The following medications were prohibited during participation in the study:

Omega-3-acid ethyl esters and omega-3-PUFA containing supplements >200 mg per day Vitamin E>60 IU per day Thiazolidinediones (e.g. pioglitazone)

The following medications were allowed during the study according to the specified restrictions:

Subjects could continue prescription or over-the-counter medications or herbal remedies (HMG-CoA reductase inhibitors [statins], fibrates, probucol, ezetimibe, ursodiol [UDCA], taurine, betaine, N-acetylcysteine, s-adenosylmethionine [SAM-e], milk thistle, anti-TNF therapies, or probiotics) ONLY if they have been on a stable dose for at least 6 months prior to screening Subjects could continue the following anti-diabetic medications if they have been taking stable doses since at least 6 months prior to liver biopsy: biguanides (metformin), insulin, sulfonylureas, alpha-glucosidase inhibitors (acarbose), and phenylalanine derivatives (nateglinide)

Any subjects receiving anti-platelet therapy or anti-thrombotic agents (e.g. warfarin, ASA, and clopidogrel) after study commencement should be monitored closely during the study Preliminary Results A) A sub-population of NASH patients were counted and classified as responders or non responders as shown in FIG. 1. Preliminary data indicated higher efficacy of the pharmaceutical composition in patients who were determined not to have diabetes or showed mild diabetes as compared to diabetic patients in Study arm 1 (600 mg EPA-E, TID). The efficacy of Study arm 2 (900 mg EPA-E, TID) was also equivalent to that of Study arm 1.

The same sub-population of patients was further characterized. HbA1c levels were measured for patients, whose HbA1c=<6.4, as shown in FIG. 2. Preliminary data indicates higher efficacy of the pharmaceutical composition in patients with HbA1c levels=<6.4 in all cases, and especially who would be classified as non-diabetic (including pre-diabetic) based on guidelines as set by the ADA and as described herein in Study arm 1. The efficacy of Study arm 2 was also equivalent to that of Study arm 1.

Diabetes in the same sub population of patients was alternatively measured using a test for fasting glucose. Glucose levels were measured for patients, whose glucose levels were =<125 mg/dL and, as shown in FIG. 3. Preliminary data indicates higher efficacy of the pharmaceutical composition in patients with =<125 mg/dL and who would be classified as non-diabetic (including pre-diabetic) or diabetic based on guidelines as set by the ADA and as described herein in Study arm 1. The efficacy of Study arm 2 was also equivalent to that of Study arm 1.

The chart in FIG. 4 indicates that taken together, non-diabetic (including pre-diabetic) or diabetic, as measured by both fasting glucose=<125 mg/dL and HbA1c=<6.4, indicated a higher response to rate to the EPA-E in Study arm 1. The efficacy of Study arm 2 was also equivalent to that of Study arm 1.

B) A second sub-population of NASH patients were counted and classified as responders or non responders as shown in FIG. 7. Preliminary data indicates higher efficacy of the pharmaceutical composition in patients who were determined not to have biliary tract disease markers associated with the disease in both Study arm 1 (600 mg EPA-E, TID) and Study arm 2 (900 mg EPA-E, TID).

γ-Glutamyl Transferase (GGT) v. Preliminary Endpoint achievement rate is reflected in FIG. 8. Preliminary data indicates higher efficacy of the pharmaceutical composition in patients with GGT levels=<60 IU/L in both Study arm 1 and 2.

The same sub-population of patients was further characterized. NASH response (change of NAS score) was measured for patients, whose GGT levels=<33 IU/L, as shown in the table of FIG. 9. Preliminary data indicates higher efficacy of the pharmaceutical composition in patients with GGT levels=<33 IU/L, and who would be classified as not having biliary duct disease in both Study arm 1 and 2.

Alternatively, improvement of serum EPA/AA ratio on Day 365 of patients with γ-Glutamyl Transferase (GGT) levels ≤33 IU/L was also measured, as shown in the table of FIG. 10. Preliminary data indicates higher efficacy of the pharmaceutical composition in patients with ≤33 IU/L and who would be classified as not biliary duct disease in Study arm 2.

The table in FIG. 11 provides corresponding reference values for parameters of liver function in patients with γ-Glutamyl Transferase (GGT) levels ≤33 IU/L and patients with γ-Glutamyl Transferase (GGT) levels ≥33 IU/L. Serum direct bilirubin levels were also assays in the sub group of patients with γ-Glutamyl Transferase (GGT) levels ≥33 IU/L/L. All patients were observed within reference (normal) value for direct bilirubin levels. The range of serum direct bilirubin of patients with serum GGT levels ≤33 IU/L was between 0.03 and 0.17.

Figure 12:
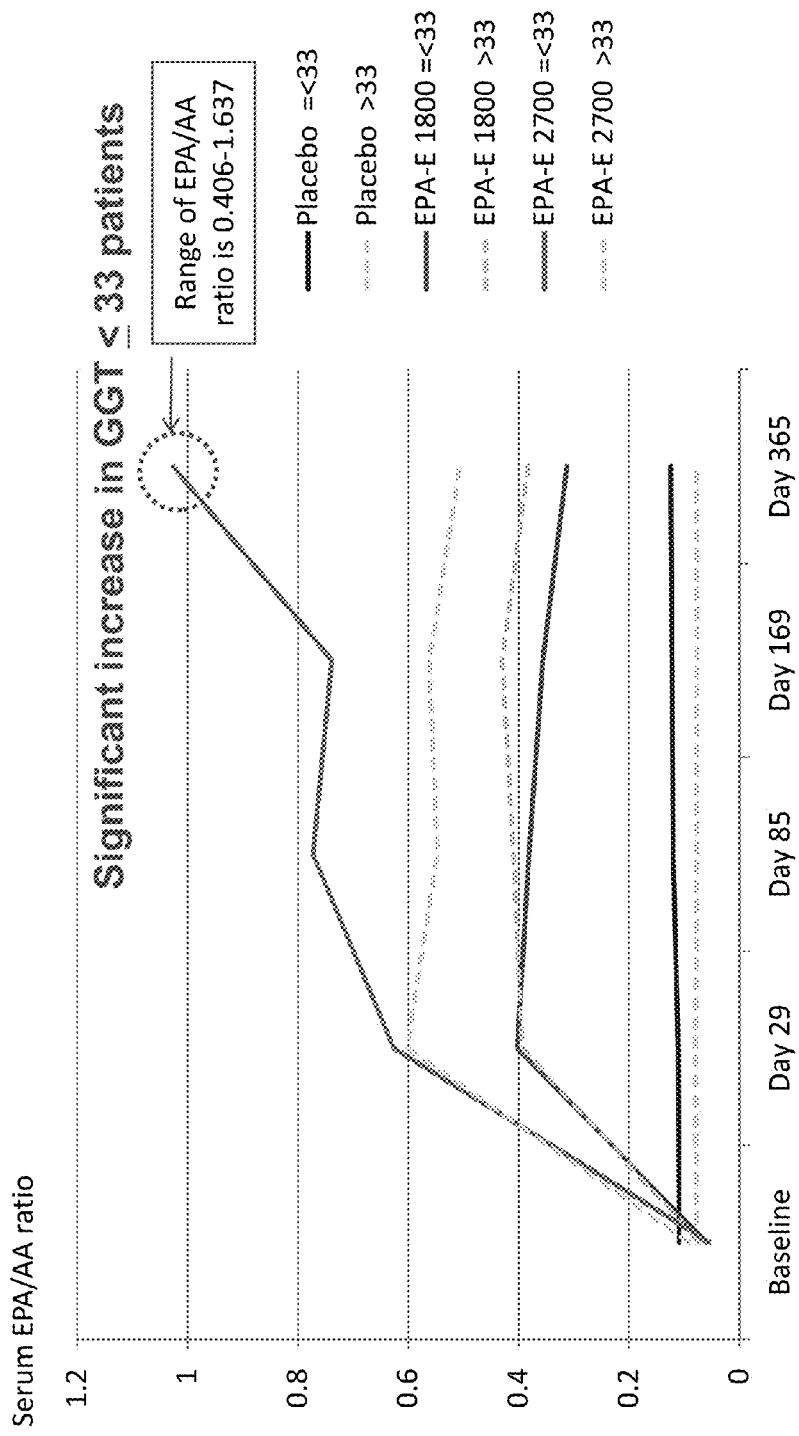
FIG. 12 is a chart representing serum EPA/AA ratios for various administered dosages of EPA-E over time.

FIG. 12 is a chart representing serum EPA/AA ratios for various administered dosages of EPA-E over time. The chart indicates a significant increase in EPA/AA ratio in patients with γ-Glutamyl Transferase (GGT) levels ≤33 IU/L in Study arm 2. The range of the improvement in this ratio on Day 365 of patients with serum GGT levels ≤33 IU/L was observed between 0.0406 and 1.637 for administered 2700 mg/day dose of EPA-E.

Figure 13:
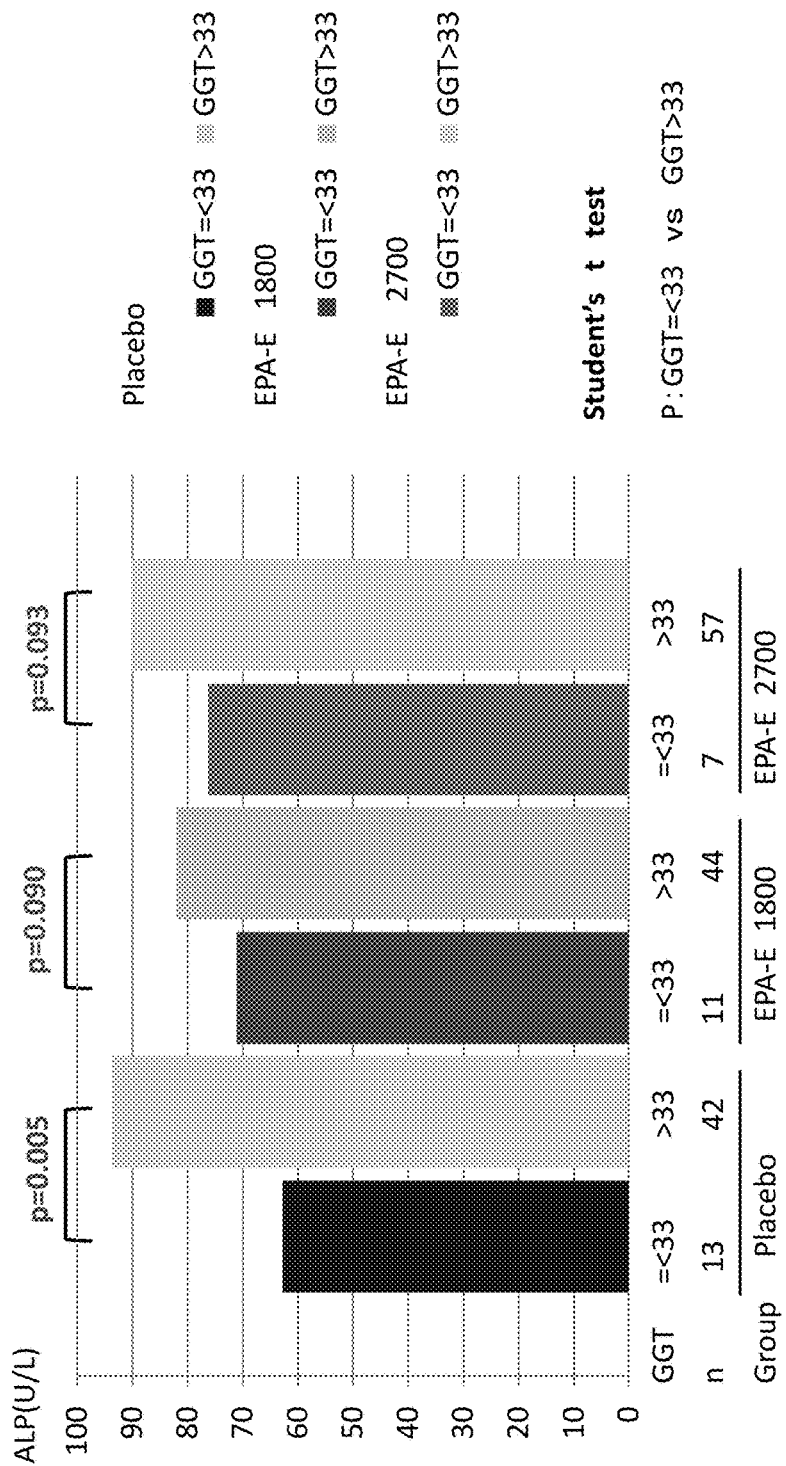
FIG. 13 is a chart representing serum ALP of patients with γ-Glutamyl Transferase (GGT) levels ≤33 IU/L.

ALP levels were also assays in the sub group of patients with γ-Glutamyl Transferase (GGT) levels ≤33 IU/L and patients with γ-Glutamyl Transferase (GGT) levels ≥33 IU/L. Some patients in GGT>=33 IU/L and placebo group showed ALP value above reference (normal) value as shown in FIG. 13.

Example 3: Self-Emulsifying Formulation 0.5 g of soybean lecithin, 1.0 g of polyoxyethylene (60) hydrogenated castor oil, 0.4 g of propylene glycol, and 3.1 g of EPA-E were weighed, and mixed while heating to a temperature of about 70° C. to prepare a self-emulsifying composition. After substituting with nitrogen, the self-emulsifying composition was hermetically sealed and stored at room temperature until the evaluation. Formulation of the self-emulsifying composition is shown below:

| Ingredients | Formulation (% by weight) |
| --- | --- |
| EPA-E | 62.0 |
| Soybean lecithin | 10.0 |
| Polyoxyethylene (60) hydrogenated castor oil | 20.0 |
| Propylene glycol | 8.0 |
| Total | 100.0 |

Example 4: Self-Emulsifying Formulation 0.5 g of soybean lecithin, 1.0 g of polyoxyethylene (50) hydrogenated castor oil, 0.4 g of propylene glycol, and 3.1 g of EPA-E were weighed, and a self-emulsifying composition was prepared and stored by repeating the procedure of Example 3. Formulation of the self-emulsifying composition is shown below:

| Ingredients | Formulation (% by weight) |
| --- | --- |
| EPA-E | 62.0 |
| Soybean lecithin | 10.0 |

| Ingredients | Formulation (% by weight) |
|---|---|
| Polyoxyethylene (60) hydrogenated castor oil | 20.0 |
| Propylene glycol | 8.0 |
| Total | 100.0 |

Example 5: Self-Emulsifying Formulation 0.5 g of soybean lecithin. 0.9 g of polyoxyethylene castor oil, 0.6 g of propylene glycol, and 3.0 g of EPA-E were weighed, and a self-emulsifying composition was prepared and stored by repeating the procedure of Example 1. Formulation of the self-emulsifying composition is shown below:

| Ingredients | Formulation (% by weight) |
|---|---|
| EPA-E | 60.0 |
| Soybean lecithin | 10.0 |
| Polyoxyethylene castor oil | 18.0 |
| Propylene glycol | 12.0 |
| Total | 100.0 |

Example 6: Self-Emulsifying Formulation 0.6 g of soybean lecithin, 0.6 g of polyoxyethylene (60) hydrogenated castor oil, 0.5 g of propylene glycol, and 3.3 g of EPA-E were weighed, and a self-emulsifying composition was prepared and stored by repeating the procedure of Example 1. Formulation of the self-emulsifying composition is shown below:

| Ingredients | Formulation (% by weight) |
|---|---|
| EPA-E | 66.0 |
| Soybean lecithin | 12.0 |
| Polyoxyethylene (60) hydrogenated castor oil | 12.0 |
| Propylene glycol | 10.0 |
| Total | 100.0 |

Example 7: Self-Emulsifying Formulation 0.5 g of soybean lecithin, 0.5 g of polyoxyethylene (50) hydrogenated castor oil, 0.5 g of propylene glycol, and 3.5 g of EPA-E were weighed, and a self-emulsifying composition was prepared and stored by repeating the procedure of Example 3. Formulation of the self-emulsifying composition is shown below:

| Ingredients | Formulation (% by weight) |
|---|---|
| EPA-E | 70.0 |
| Soybean lecithin | 10.0 |
| Polyoxyethylene (50) hydrogenated castor oil | 10.0 |
| Propylene glycol | 10.0 |
| Total | 100.0 |

Example 8: Self-Emulsifying Formulation 0.3 g of soybean lecithin, 0.3 g of polyoxyethylene (20) sorbitan monooleate, 0.9 g of polyoxyethylene (60) hydrogenated castor oil, 0.4 g of propylene glycol, and 3.1 g of EPA-E were weighed, and a self-emulsifying composition was prepared and stored by repeating the procedure of Example 3. Formulation of the self-emulsifying composition is shown below:

| Ingredients | Formulation (% by weight) |
|---|---|
| EPA-E | 62.0 |
| Soybean lecithin | 6.0 |
| Polyoxyethylene (20) sorbitan monooleate | 6.0 |
| Polyoxyethylene (60) hydrogenated castor oil | 18.0 |
| Propylene glycol | 8.0 |
| Total | 100.0 |

What is claimed is:

1. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject,
   wherein the subject has a serum gamma glutamyl transferase (GGT) activity level higher than 33 IU/L before the treatment,
   wherein the treatment results in a reduction of 1% to about 90% of alkaline phosphatase (ALP) concentration in the subject, and
   wherein the pharmaceutical composition comprises a polyhydric alcohol that is glycerin, propylene glycol, ethyleneglycol, trimethylene glycol, 1,2-butylene glycol, tetramethylene glycol, 1,3-butylene glycol, 2,3-butylene glycol, pentamethylene glycol, trimethylolpropane, 1,2,6-hexane triol, diethylene glycol, dipropylene glycol, triethylene glycol, polyethylene glycol, polypropylene glycol, polyglycerin, or a combination thereof.

2. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject,
   wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises 5% to 50% by weight of emulsifiers having a hydrophilic lipophilic balance of at least 10, wherein the emulsifiers are i) polyoxyethylene sorbitan fatty acid ester, and ii) polyoxyethylene hydrogenated castor oil and/or polyoxyethylene castor oil.

3. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises 5% to 50% by weight of emulsifiers, wherein the emulsifiers are polyoxyethylene sorbitan fatty acid ester and sorbitan fatty acid ester.

4. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the administering treatment, wherein the treatment results in a reduction of 1% to about 90% of alkaline phosphatase (ALP) concentration in the subject, and wherein the pharmaceutical composition comprises 1% to 20% by weight in a total amount of the pharmaceutical composition of a sucrose fatty acid ester having a hydrophilic lipophilic balance of less than 10 and 3 to 40 parts by weight of a glycerin based on 100 parts by weight of the EPA, the EPA-E, or the pharmaceutically acceptable salt thereof.

5. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises a polyoxyethylene sorbitan fatty acid ester that is polyoxyethylene (20) sorbitan monolaurate, polyoxyethylene (20) sorbitan monopalmitate, polyoxyethylene (20) sorbitan monostearate, polyoxyethylene (20) sorbitan tristearate, polyoxyethylene (20) sorbitan monoisostearate, polyoxyethylene (20) sorbitan monooleate, polyoxyethylene (20) sorbitan trioleate, or a combination thereof.

6. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises a polyoxyethylene hydrogenated castor oil that is polyoxyethylene (20) hydrogenated castor oil, polyoxyethylene (40) hydrogenated castor oil, polyoxyethylene (50) hydrogenated castor oil, polyoxyethylene (60) hydrogenated castor oil, polyoxyethylene (100) hydrogenated castor oil, or a combination thereof.

7. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises a polyoxyethylene castor oil that is NIKKOL CO-3 with an average ethylene oxide mole number of 3, NIKKOL CO-10 with an average ethylene oxide mole number of 10, EMALEX C-20 with an average ethylene oxide mole number of 20, EMALEX C-30 with an average ethylene oxide mole number of 30, EMALEX C-40 with an average ethylene oxide mole number of 40, EMALEX C-50 with an average ethylene oxide mole number of 50, or a combination thereof.

8. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject, wherein the subject has a serum gamma glutamyl transferase (GGT) activity level higher than 33 IU/L before the treatment, wherein the treatment results in a reduction of 1% to about 90% of alkaline phosphatase (ALP) concentration in the subject, and wherein the pharmaceutical composition comprises a polyethylene glycol fatty acid ester that is polyethylene glycol monolaurate, polyethylene glycol monostearate, polyethylene glycol monooleate, polyethylene glycol distearate, polyethylene glycol diisostearate, or a combination thereof.

9. A method for treating a subject in a population of humans having a non-alcoholic fatty liver disease (NAFLD)

or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject,
- wherein the subject has a serum gamma glutamyl transferase (GGT) activity level higher than 33 IU/L before the administering treatment,
- wherein the treatment results in a reduction of 1% to about 90% of alkaline phosphatase (ALP) concentration in the subject, and
- wherein the pharmaceutical composition comprises a polyoxyethylene polyoxypropylene glycol that is polyoxyethylene (3) polyoxypropylene (17) glycol, polyoxyethylene (20) polyoxypropylene (20) glycol, polyoxyethylene (42) polyoxypropylene (67) glycol, polyoxyethylene (54) polyoxypropylene (39) glycol, polyoxyethylene (105) polyoxypropylene (5) glycol, polyoxyethylene (120) polyoxypropylene (40) glycol, polyoxyethylene (160) polyoxypropylene (30) glycol, polyoxyethylene (196) polyoxypropylene (67) glycol, polyoxyethylene (200) polyoxypropylene (70) glycol, or a combination thereof.

10. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject,
- wherein the subject has a serum gamma glutamyl transferase (GGT) activity level higher than 33 IU/L before the treatment,
- wherein the treatment results in a reduction of 1% to about 90% of alkaline phosphatase (ALP) concentration in the subject, and
- wherein the pharmaceutical composition comprises a sucrose fatty acid ester that is Surfhope SE PHARMA J-1216 containing 95% of lauric acid in the fatty acid, Surfhope SE PHARMA J-1416 containing 95% of myristic acid in the fatty acid, Surfhope SE PHARMA J-1615 or J-1616 containing 80% of palmitic acid in the fatty acid, J-1811, J-1815, or J-1816 containing 70% of stearic acid in the fatty acid, Surfhope SE PHARMA J-1715 containing 70% of oleic acid in the fatty acid, or a combination thereof.

11. A method for treating a subject in a population of humans having a non-alcoholic fatty liver disease (NAFLD) or a non-alcoholic steatohepatitis (NASH), comprising administering a therapeutically effective amount of a pharmaceutical composition that comprises eicosapentaenoic acid (EPA), ethyl eicosapentanoate (EPA-E), or a pharmaceutically acceptable salt thereof to the subject,
- wherein the subject has a serum gamma glutamyl transferase (GGT) activity level higher than 33 IU/L before the treatment,
- wherein the treatment results in a reduction of 1% to about 90% of alkaline phosphatase (ALP) concentration in the subject, and
- wherein the pharmaceutical composition comprises a lecithin that is soybean lecithin, enzymatically decomposed soybean lecithin, hydrogenated soybean lecithin, egg yolk lecithin, hydrogenated phospholipid, phospholipid from milk, lysolecithin, phosphatidyl choline, phosphatidyl serine, or a combination thereof.

12. The method of any one of claims 1-11, wherein the eicosapentaenoic acid (EPA), the ethyl eicosapentanoate (EPA-E), or the pharmaceutically acceptable salt thereof ranges from about 1800 mg to about 2700 mg per day.

13. The method of any one of claims 1-11, wherein the pharmaceutical composition is in a dosage form of a capsule.

14. The method of any one of claims 1-11, wherein the subject has NASH before the treatment.

* * * * *